(12) United States Patent
Ferrara et al.

(10) Patent No.: US 7,709,455 B2
(45) Date of Patent: May 4, 2010

(54) COMPOSITIONS AND METHODS FOR LIVER GROWTH AND LIVER PROTECTION

(75) Inventors: Napoleone Ferrara, San Francisco, CA (US); Kenneth J Hillan, San Francisco, CA (US); Jennifer Le Couter, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 217 days.

(21) Appl. No.: 11/535,049

(22) Filed: Sep. 25, 2006

(65) Prior Publication Data

US 2007/0122394 A1 May 31, 2007

Related U.S. Application Data

(63) Continuation of application No. 10/455,470, filed on Jun. 5, 2003.

(60) Provisional application No. 60/386,637, filed on Jun. 5, 2002.

(51) Int. Cl.
| | |
|---|---|
| *A01N 43/04* | (2006.01) |
| *C12Q 1/68* | (2006.01) |
| *C12N 15/88* | (2006.01) |
| *C07H 21/02* | (2006.01) |
| *C07H 21/04* | (2006.01) |

(52) U.S. Cl. .............. 514/44; 435/6; 435/91.1; 435/455; 435/458; 536/23.1; 536/23.5

(58) Field of Classification Search ............ 435/6, 435/91.1, 455, 458; 514/1, 2, 44; 536/23.1, 536/23.5; 530/350
See application file for complete search history.

(56) References Cited

U.S. PATENT DOCUMENTS

| | | | |
|---|---|---|---|
| 5,217,999 A | 6/1993 | Levitzki et al. | |
| 5,227,158 A | 7/1993 | Jardieu | |
| 5,302,606 A | 4/1994 | Spada et al. | |
| 5,330,992 A | 7/1994 | Eissenstat et al. | |
| 6,057,428 A | 5/2000 | Keyt et al. | |
| 6,100,071 A | 8/2000 | Davis-Smyth et al. | |
| 6,107,046 A | 8/2000 | Alitalo et al. | |
| 6,576,608 B1 | 6/2003 | Lee et al. | |
| 2002/0164310 A1* | 11/2002 | Flugelman et al. | 424/93.21 |
| 2003/0096754 A1 | 5/2003 | Pollitt et al. | |
| 2004/0116343 A1 | 6/2004 | Flugelman et al. | |

FOREIGN PATENT DOCUMENTS

| | | |
|---|---|---|
| EP | 0 566 226 A1 | 10/1993 |
| WO | WO 91/15495 | 10/1991 |
| WO | WO 92/21660 | 12/1992 |
| WO | WO 94/03427 | 2/1994 |
| WO | WO 94/14808 | 7/1994 |
| WO | WO 97/08313 | 3/1997 |
| WO | WO 00/63380 | 10/2000 |

OTHER PUBLICATIONS

Ferrara, N. et al., Endocrine Reviews, vol. 18, No. 1, pp. 4-25 (1998).*
Achen et al., "Vascular endothelial growth factor D (VEGF-D) is a ligand for the tyrosine kinases VEGF receptor 2 (Flk1) and VEGF receptor 3 (Flt4)" *Proc. Natl. Acad. Sci. USA* 95(2):548-553 (Jan. 20, 1998).
Adamis et al., "Inhibition of Vascular Endothelial Growth Factor Prevents Retinal Ischemia-Associated Iris Neovascularization in a Nonhuman Primate" *Arch. Ophthalmology* 114(1):66-71 (1996).
Aiello et al., "Vascular endothelial growth factor in ocular fluid of patients with diabetic retinopathy and other retinal disorders" *New England J. of Medicine* 331(22):1480-1487 (1994).
Ajioka et al., "Expression of Vascular Endothelial Growth Factor Promotes Colonization, Vascularization, and Growth of Transplanted Hepatic Tissues in the Mouse" *Hepatology* 29:396-402 (1999).
Assy et al., "Effect of vascular edothelial growth factor on hepatic regenerative activity following partial hepatectomy in rats" *Journal of Hepatology* 30:911-915 (1999).
Ayelet, S. et al, "Hemodynamic forces act as primary stimulus for liver regeneration." *FASEB J.* 16(4) :A201 (Apr. 2002).
Barleon et al., "Migration of Human Monocytes in Response to Vascular Endothelial Growth Factor (VEGF) Is Mediated via the VEGF Receptor flt-1" *Blood* 87:3336-3343 (1996).
Baruch et al., "Basic fibroblast growth factor is hepatotropic for rat liver in regeneration" *J. Hepatol.* 23:328-332 (1995).
Berkman et al., "Expression of the vascular permeability factor/vascular endothelial growth factor gene in central nervous system neoplasms" *J. Clin. Invest.* 91(1):153-159 (1993).

(Continued)

*Primary Examiner*—Jane Zara
(74) *Attorney, Agent, or Firm*—Jones Day

(57) ABSTRACT

The present invention provides pharmaceutical compositions and methods for liver proliferation and protection. Specifically useful are VEGFR modulating agents capable of promoting liver growth. Disclosed compositions and methods may be useful for promoting proliferation or treating pathological conditions in other organs of significant biological functions.

14 Claims, 8 Drawing Sheets

OTHER PUBLICATIONS

Borgstrom et al., "Complete inhibition of angiogenesis and growth of microtumors by anti-vascular endothelial growth factor neutralizing antibody: novel concepts of angiostatic therapy from intravital videomicroscopy" *Cancer Research* 56(17):4032-4039 (Sep. 1, 1996).

Brown et al., "Expression of vascular permeability factor (vascular endothelial growth factor) and its receptors in adenocarcinomas of the gastrointestinal tract" *Cancer Research* 53(19):4727-4735 (1993).

Brown et al., "Expression of vascular permeability factor (vascular endothelial growth factor) and its receptors in breast cancer" *Human Pathology* 26(1):86-91 (1995).

Carmeliet et al., "Abnormal blood vessel development and lethality in embryos lacking a single VEGF allele" *Nature* 380(6573):435-438 (Apr. 4, 1996).

Conn et al., "Amino acid and cDNA sequences of a vascular endothelial cell mitogen that is homologous to platelet-derived growth factor" *Proc. Natl. Acad. Sci. USA* 87:2628-2632 (1990).

Cornelius, C., "Liver Function Tests in the Differential Diagnosis of Hepatotoxicity" *Hepatotoxicology*, Meeks et al., Chapter 5, pp. 181-185 (1991).

de Vries et al., "The fms-like tyrosine kinase, a receptor for vascular endothelial growth factor" *Science* 255:989-991 (1992).

Dellian et al., "Technical Advance. Quantitation and Physiological Characterization of Angiogenic Vessels in Mice" *Am. J. Pathol.* 149:59-71 (1996).

Drakes et al., "In Vivo Administration of flt3 Ligand Markedly Stimulates Generation of Dendritic Cell Progenitors from Mouse Liver" *J. Immunol.* 159:4268-4278 (1997).

Dvorak et al., "Vascular permeability factor/vascular endothelial growth factor, microvascular hyperpermeability, and angiogenesis" *American Journal of Pathology* 146(5):1029-1039 (1995).

Ferrara and Davis-Smyth, "The Biology of Vascular Endothelial Growth Factor" *Endocrine Reviews* 18(1):4-25 (1997).

Ferrara and Henzel, "Pituitary Follicular Cells Secrete a Novel Heparin-binding Growth Factor Specific for Vascular Endothelial Cells" *Biochem. & Biophys. Res. Comm.* 161(2):851-858 (1989).

Ferrara et al., "Heterozygous embryonic lethality induced by targeted inactivation of the VEGF gene" *Nature* 380(6573):439-442 (Apr. 4, 1996).

Ferrara et al., "Role of vascular endothelial growth factor in the regulation of angiogenesis" *Kidney International* 56:794-814 (1999).

Ferrara et al., "Vascular endothelial growth factor is essential for corpus lutem angiogenesis" *Nature Med.* 4:336-340 (1998).

Ferrara, N., "Molecular and biological properties of vascular endothelial growth factor" *J Mol Med* 77:527-543 (1999).

Ferrara, N., "Vascular endothelial growth factor. The trigger for neovascularization in the eye" *Laboratory Investigation* 72(6):615-618 (1995).

Folkman and Klagsbrun, "Angiogenic factors" *Science* 235:442-447 (1987).

Folkman., "Angiogenesis in Cancer, Vascular, Rheumatoid and Other Disease." *Nature Medicine* 1(1):27-31 (1995).

Fong et al., "Increased hemangioblast commitment, not vascualr disorganization, is the primary defect in flt-1 knock-out mice" *Development* 126:3015-3025 (1999).

Fujiwara et al., "Stimulation of Liver Growth by Exogenous Human Hepatocyte Growth Factor in Normal and PArtially Hepatectomized Rats" *Hepatol.* 18:1443-1449 (1993).

Gerber et al., "VEGF couples hypertrophic cartilage remodeling, ossification and angiogenesis during endochondral bone formation" *Nature Medecine* 5:623-628 (1999).

Gerber at al., "VEGF is required for growth and survival in neonatal mice" *Development* 126:1149-1159 (1999).

Gherardi and Stoker, "Hepatocytes and scatter factor" *Nature* 346:228 (1990).

Gille et al., "A repressor sequence in the juxtamembrane domain of Flt-1 (VEGFR-1) constitutively inhibits vascular endothelial growth factor-dependent phosphatidylinositol 3'-kinase activation and endothelial cell migration" *EMBO Journal* 19:4064-4073 (2000).

Gille et al., "Analysis of Biological Effects and Signaling Properties of Flt-1 (VEGFR-1) and KDR (VEGFR-2)" *Journal of Biological Chemistry* 276:3222-3230 (2001).

Guerrin et al., "Vasculotropin/Vascular Endothelial Growth Factor Is an Autocrine Growth Factor for Human Retinal Pigment Epithelial Cells Cultured In Vitro" *J. Cellular Physiology* 164:385-394 (1995).

Harman et al., "Isolation of Hepatocytes from Postnatal Mice" *J. Pharmacol. Methods* 17:157-163 (1987).

Horimoto et al., "Expression and phosphporylation of rat c-met/hepatocyte growth factor receptor during rat liver regeneration" *Journal of Hepatology* 23:174-183 (1995).

Houck et al., "The Vascular Endothelial Growth Factor Family: Identification of a Fourth Molecular Species and Characterization of Alternative Splicing of RNA" *Mol. Endocrinol.* 5(12):1806-1814 (1991).

Hu et al., "Expression of Hepatocyte Growth Factor and c-met Genes during Hepatic Differentiation and Liver Development in the Rat" *Am. J. Pathol.* 142:1823-1830 (1993).

Ito et al., "Heparin-Binding EGF-like Growth Factor is a Potent Mitogen for Rat Hepatocytes" *Biochem. & Biophys. Res. Comm.* 198:25-31 (1994).

Jakeman et al., "Binding Sites for Vascular Endothelial Growth Factor Are Localized on Endothelial Cells in Adult Rat Tissues" *J. Clin. Invest.* 89:244-253 (1992).

Jeltsch et al., "Hyperplasia of Lymphatic Vessels in VEGF-C Transgenic Mice" *Science* 276:1423-1425 (1997).

Joukov et al., "A novel vascular endothelial growth factor, VEGF-C, is a ligand for the Flt4 (VEGFR-3) and KDR (VEGF-2) receptor tyrosine kinases" *EMBO Journal* 15:1751 (1996).

Kendall et al., "Identification of a Natural Soluble Form of the Vascular Endothelial Growth Factor Receptor, FLT-1, and Its Heterodimerization with KDR" *Biochem. & Biophys. Res. Comm.* 226:324-328 (1996).

Keyt et al., "Identification of Vascular Endothelial Growth Factor Determinants for Binding KDR and FLT-1 Receptors: Generation of Receptor-Selective VEGF Variants by Site-Directed Mutagenesis." *Journal of Biological Chemistry* 271(10):5638-5646 (1996).

Kim et al., "Inhibition of Vascular Endothelial Growth Factor-Induced Angiogenesis Suppresses Tumour Growth in vivo" *Nature* 362:841-844 (Apr. 29, 1993).

Kliche and Waltenberger, "VEGF Receptor Signaling and Endothelial Function" *IUBMB Life* 52:61-66 (2001).

Koch et al., "Hepatocyte Growth Factor. A Cytokine Mediating Endothelial Migration in Inflammatory Arthritis" *Arthr. Rheum.* 39:1566-1575 (1996).

Kroll and Waltenberger, "The Vascular Endothelial Growth Factor Receptor KDR Activates Multiple Signal Transduction Pathways in Porcine Aortic Endothelial Cells" *Journal of Biological Chemistry* 272:32521-32527 (1997).

Lammert et al., "Induction of Pancreatic Differentiation by Signals from Blood Vessels" *Science* 294:564-567 (2001).

LeCouter et al., "Identification of an angiogenic mitogen selective for endocrine gland endothelium" *Nature* 412:877-884 (2001).

Lee et al., "Vascular endothelial growth factor-related protein: A ligand and specific activator of the tyrosine kinase receptor Flt4" *Proc. Natl. Acad. Sci. USA* 93:1988-1992 (1996).

Leenen et al., "Markers of mouse macrophage development detected by monocolonal antobodies" *J. Immunol. Methods* 174:5-19 (1994).

Leung et al., "Vascular Endothelial Growth Factor is a Secreted Angiogenic Mitogen" *Science* 246:1306-1309 (Dec. 1989).

Li et al., "Receptor-selective Variants of Human Vascular Endothelial Growth Factor " *Journal of Biological Chemistry* 275:29823-29828 (2000).

Lopez et al., "Transdifferentiated retinal pigment epithelial cells are immunoreactive for vascular endothelial growth factor in surgically excised age-related macular degeneration-related choroidal neovascular membranes" *Invest. Ophthalmol. Vis. Sci.* 37(5):855-868 (1996).

Lucas, et al., "High-Level Production of Recombinant Proteins in CHO Cells Using a Dicistronic DHFR Intron Expression Vector" *Nucleic Acids Research* 24(9):1774-1779 (1996).

Lyden et al., "Impaired recruitment of bone-morrow-derived endothelial and hematopoietic precursor cells block tumor angiogenesis and growth" *Nat. Med.* 7:1194-1201 (2001).

Maglione et al., "Two alternative mRNAs coding for the angiogenic factor, placenta growth faactor (PlGF), are transcribed from a single gene of chromosome 14" *Oncogene* 8:925-931 (1993).

Matsumoto et al., "Liver Organogenesis Promoted by Endothelial Cells Prior to Vascular Function" *Science* 294:559-563 (2001).

Mattern et al., "Association of vascular endothelial growth factor expression with intratumoral microvessel density and tumour cell proliferation in human epidermoid lung carcinoma" *Brit. J. Cancer* 73(7):931-934 (1996).

Matthews et al., "A Receptor Tyrosine Kinase cDNA Isolated from a Population of Enriched Primitive Hematopoietic Cells and Exhibiting Close Genetic Linkage to c-kit." *Proc. Natl. Acad. Sci.* 88:9026-9030 (1991).

Melnyk et al., "Vascular endothelial growth factor promotes tumor dissemination by a mechanism distinct from its effect on primary tumor growth" *Cancer Research* 56(4):921-924 (Feb. 15, 1996).

Meyer et al., "A Novel Vascular Endothelial Growth Factor Encoded by Orf Virus, VEGF-E, Mediates Angiogenesis Via Signalling Through VEGFR-2 (KDR) but not VEGFR-1 (Flt-1) Receptor Tyrosine Kinases." *EMBO Journal* 18(2):363-374 (Jan. 15, 1999).

Michalopoulos and DeFrances, "Liver Regeneration" *Science* 276:60-65 (1997).

Mochida et al., "Increased Expressions of Vascular Endothelial Growth Factor and Its Receptors, flt-1 and KDR/flk-1, in Regenerating Rat Liver" *Biochem. & Biophys. Res. Comm.* 226:176-179 (1996).

Nakamura et al., "Molecular Cloning and Expression of Human Hepatocyte Growth Factor" *Nature* 342:440-443 (Nov. 23, 1989).

Nakamura et al., "Partial Purification and Characterization of Hepatocyte Growth Factor from Serum of Hepatectomized Rats" *Biochem. & Biophys. Res. Comm.* 122:1450-1459 (Aug. 16, 1984).

Nakamura et al., "Purification and Subunit Structure of Hepatocyte Growth Factor from Rat Platelets" *FEBS Letters* 224(2):311-316 (Nov. 1987).

Oberg-Welsh et al., "Effects of vascular endothelial growth factor on pancreatic duct cell replication and the insulin production of fetal islet-like cell clusters in vitro" *Mol. Cell. Endrocrinol.* 126:125-132 (1997).

Ogawa et al., "A Novel Type of Vascular Endothelial Growth Factor, VEGF-E (NZ-7 VEGF), Preferentially Utilizes KDR/Flk-1 Receptor and Carries a Potent Mitotic Activity Without Heparin-Binding Domain." *J. Bio. Chem.* 273(47):31273-31282 (Nov. 20, 1998).

Olofsson et al., "Vascular Endothelial Growth Factor B (VEGF-B) Binds to VEGF Receptor-1 and Regulates Plasminogen Activator Activity in Endothelial Cells." *Proc. Natl. Acad. Sci. USA* 95(20):11709-11714 (Sep. 29, 1998).

Olofsson et al., "Vascular endothelial growth factor B, a novel growth factor for endothelial cells" *Proc. Natl. Acad. Sci. USA* 93:2576-2581 (1996).

Omori et al., "Partial Cloning of Rat CD34 cDNA and Expression During Stem Cell-Dependent Liver Regeneration in the Adult Rat" *Hepatology* 26:720-727 (1997).

Park et al., "Placenta growth factor. Potentiation of vascular endothelial growth factor bioactivity, in vitro and in vivo, and high affinity binding to Flt-1 but not to Flk-1/KDR" *Journal of Biological Chemistry* 269(41):25646-25654 (1994).

Patijn et al., "Hepatocyte Growth Factor Induces Hepatocyte Proliferation In Vivo and Allows for Efficient Retroviral-Mediated Gene Transfer in Mice" *Hepatol.* 28:707-716 (1998).

Plouet et al., "Isolation and characterization of a newly identified endothelial cell mitogen produced by AtT-20 cells" *EMBO Journal* 8(12):3801-3806 (1989).

Rodgers et al., "Histologic Alterations in Dermal Repair after Thermal Injury Effects of Topical Angiotensin II" *J. Burn Care Rehabil.* 18:381-388 (1997).

Rodriguez et al., "A Sensitive Fluorometric Enzyme-Linked Immunosorbent Assay That Measures Vascular Endothelial Growth Factor$_{165}$ In Human Plasma." *J. Immunol. Methods* 219:45-55 (1998).

Roos et al., "Induction of Liver Growth in Normal Mice by Infusion of Hepatocyte Growth Factor/Scatter Factor" *Am. J. Physiol.* 268:G380-G386 (1995).

Rosen and Goldberg, "Regulation of angiogenesis by scatter factor" *Regulation of Angiogenesis* pp. 193-208 (1997).

Ross, M.A. et al, "Spatiotemporal expression of Angiogenesis Growth Factor Receptors During the Revascularization of Regenerating Rat Liver" *Hepatology* 34(6):1135-1148 (Dec. 2001).

Russell et al., "Partial Characterization of a Hepatocyte Growth Factor From Rat Platelets" *J. Cellular Physiology* 119:183-192 (1984).

Sakata et al., "Hepatocyte Growth Factor/Scatter Factor Overexpression Induces Growth, Abnormal Development, and Tumor Formation in Transgenic Mouse Livers" *Cell Growth Differ.* 7:1513-1523 (1996).

Schlessinger and Ullrich, "Growth factor signaling by receptor tyrosine kinases" *Neuron* 9:383-391 (1992).

Schmidt et al., "Scatter factor/hepatocyte growth factor is essential for liver development" *Nature* 373:699-702 (Feb. 23, 1995).

Shibuya et al., "Nucleotide Sequence and Expression of a Novel Human Receptor-Type Tyrosine Kinase Gene (flt) Closely Related to the fms Family." *Oncogene* 5:519-524 (1990).

Shiota et al., "Hepatocyte Growth Factor in Transgenic Mice: Effects on Hepatocyte Growth, Liver Regeneration and Gene Expression" *Hepatol.* 19:962-972 (1994).

Soker et al., "Neuropilin-1 is Expressed by Endothelial and Tumor Cells as an Isoform-Specific Receptor for Vascular Endothelial Growth Factor." *Cell.* 92:735-745 (Mar. 1998).

Sondell et al., "Vascular Endothelial Growth Factor Has Neurotropic Activity and Stimulates Axonal Outgrowth, Enhancing Cell Survival and Schwann Cell Proliferation in the Peripheral Nervous System" *J. Neurosci* 19:5731-5740 (1999).

Stoker and Perryman, "An Epithelial Scatter Factor Released by Embryo Fibroblasts" *J. Cell. Sci.* 77:209-223 (1985).

Sugimoto et al., "Cloning and Characterization of the Hakata Antigen, a Member of the Ficolin/Opsonin p35 Lectin Family" *Journal of Biological Chemistry* 273(33):20721-20727 (Aug. 14, 1998).

Suzuma et al., "Vascular Endothelial Growth Factor Induces Expression of Connective Tissue Growth Factor via KDR, Flt1, and Phosphatidylinositol 3-Kinase-Akt-dependent Pathways in Retinal Vascular Cells" *Journal of Biological Chemistry* 275:40725-40731 (2000).

Terman et al., "Identification of a New Endothelial Cell Growth Factor Receptor Tyrosine Kinase." *Oncogene.* 6:1677-1683 (1991).

Terman et al., "Identification of the KDR Tyrosine Kinase as a Receptor for Vascular Endothelial Cell Growth Factor." *Biochem. & Biophys. Res. Comm.* 187:1579-1586 (1992).

Thurston et al., "Angiopoietin-1 protects the adult vasculature against plasma leakage" *Nat. Med.* 6:460-463 (2000).

Ullrich and Schlessinger, "Signal Transduction by Receptors with Tyrosine Kinase Activity" *Cell* 61:203-212 (Apr. 1990).

Urlaub and Chasin, "Isolation of Chinese Hamster Cell Mutants Deficient in Dihydrofolate Reductase Activity" *Proc. Natl. Acad. Sci. USA* 77(7):4216 (Jul. 1980).

Vande Woude et al., "The Hepatocyte Growth Factor/ Met Pathway in Development, Tumorigenesis, and B-Cell Differentiation" *Adv. Cancer Res.* 79:39-90 (2000).

Warren et al., "Regulation by vascular endothelial growth factor of human colon cancer tumorigenesis in a mouse model of experimental liver metastasis" *J. Clin. Invest.* 95(4):1789-1797 (Apr. 1995).

Wong et al., "Excessive tumor-elaborated VEGF and its neutralization define a lethal paraneoplastic syndrome" *Proc. Natl. Acad. Sci. USA* 98:7481-7486 (2001).

Yamane et al., "A new communication system between hepatocyte and sinusoidal endothelial cells in liver through vascular endothelial growth factor and Flt tyrosine kinase receptor family (Flt-1 and KDR/Flk-1)" *Oncogene* 9:2683-2690 (1994).

Yang et al., "Substantially attenuated hemodynamic responses to *Escherichia coli*-derived vascular endothelial growth factor given by intravenous infusion compared with bolus injection" *J. Pharm. Exp. Ther.* 284(1):103-110 (1998).

Yarden et al., "Growth Factor Receptor Tyrosine Kinases" *Ann. Rev. Biochem.* 57:443-478 (1988).

Zeng et al., "Vascualr Permeability Factor (VPF) / Vascular Endothelial Growth Factor (VEGF) Receptor-1 Down-modulates VPF/VEGF Receptor-2-mediated Endothelial Cell Proliferation, but not Migration, through Phosphatidylinositol 3-Kinase-dependent Pathways" *Journal of Biological Chemistry* 276:26969-26979 (2001).

Zioncheck et al., "Sulfated Oligosaccharides Promote Hepatocyte Growth Factor Association and Govern Its Mitogenic Activity" *Journal of Biological Chemistry* 270:16871-16878 (1995).

Zioncheck et al., "The Pharmacokinetics, Tissue Localization, and Metabolic Processing of Recombinant Human Hepatocyte Growth Factor after Intravenous Administration in Rats" *Endocrinology* 134:1879-1887 (1994).

Agrawal, S., et al., "Antisense Therapeutics: is it as simple as complementary base recognition?" *Molecular Med. Today* 6:72-81 (2000).

Branch, A., "A good antisense molecule is hard to find" *Trends in Biochem* 23:45-50 (1998).

Chirila, et al. *Biomaterials* 23:321-342 (2002).

Crooke, S. *Antisense Res. and Application*, Chapter 1, pp. 1-50 (1998).

Peracchi, Alessio, "Prospects for antiviral ribozymes and deoxyribozymes" *Rev. Med. Virol* 14:47-64 (2004).

Bruns et al., Vascular Endothelial Growth Factor is an In Vivo Survival Factor for Tumor Endothelium in a Murine Model of Colorectal Carcinoma Liver Metastases, Caner, 89(3): 488-499 (2000).

European Search Report dated May 6, 2009 for European patent application No. 03757334.2.

LeCouter et al., Angiogenesis-Independent Endothelial Protection of Liver: Role of VEGFR-1, Scienc, 299(5608): 890-893 (2003).

Neufeld et al., "Vascular endothelial growth factor (VEGF) and its receptors," The FAEBS Journal, 13: 9-22 (1999).

Snir et al, "Hemodynamic forces act as a primary stimulus for liver regeneration," FASEB J., 16(4): A201 (2002).

Taniguchi et al., "Expression and Role of Vascular Endothelial Growth Factor in Liver Regeneration After Partial Hepatectomy in Rats," The Journal of Histochemistry & Cytochemistry, 49: 121-129 (2001).

* cited by examiner

SEQUENCE LISTING

```
<160> NUMBER OF SEQ ID NOS: 36

<210> SEQ ID NO 1
<211> LENGTH: 25
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: mGAPDH forward

<400> SEQUENCE: 1
atgttccagt atgactccac tcacg                                              25

<210> SEQ ID NO 2
<211> LENGTH: 25
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: mGAPDH reverse

<400> SEQUENCE: 2
gaagacacca gtagactcca cgaca                                              25

<210> SEQ ID NO 3
<211> LENGTH: 29
<212> TYPE: DNA
<213> ORGANISM: Artificial sequence
<220> FEATURE:
<223> OTHER INFORMATION: sequence is synthesized
<220> FEATURE:
<221> NAME/KEY: PCR probe
<222> LOCATION: Full
<223> OTHER INFORMATION: mGAPDH probe

<400> SEQUENCE: 3
aagcccatca ccatcttcca ggagcgaga                                          29

<210> SEQ ID NO 4
<211> LENGTH: 20
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: HGF forward
```

```
<400> SEQUENCE: 4
ggcaaggtga ctttgaatga                                                    20

<210> SEQ ID NO 5
<211> LENGTH: 20
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: HGF reverse

<400> SEQUENCE: 5
cacatggtcc tgatccaatc                                                    20

<210> SEQ ID NO 6
<211> LENGTH: 25
<212> TYPE: DNA
<213> ORGANISM: Artificial sequence
<220> FEATURE:
<223> OTHER INFORMATION: sequence is synthesized
<220> FEATURE:
<221> NAME/KEY: PCR probe
<222> LOCATION: Full
<223> OTHER INFORMATION: HGF probe

<400> SEQUENCE: 6
tttcagcccc agcacataac tcaga                                              25

<210> SEQ ID NO 7
<211> LENGTH: 17
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: HB-EGF forward

<400> SEQUENCE: 7
tgctgccgtc ggtgatg                                                       17

<210> SEQ ID NO 8
<211> LENGTH: 16
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: HB-EGF reverse

<400> SEQUENCE: 8
accggtcacc aacgcg                                                        16

<210> SEQ ID NO 9
<211> LENGTH: 26
<212> TYPE: DNA
<213> ORGANISM: Artificial sequence
<220> FEATURE:
<223> OTHER INFORMATION: sequence is synthesized
<220> FEATURE:
<221> NAME/KEY: PCR probe
<222> LOCATION: Full
<223> OTHER INFORMATION: HB-EGF probe
```

<400> SEQUENCE: 9
tgaagctctt tctggccgca gtgttg                                                                          26

<210> SEQ ID NO 10
<211> LENGTH: 21
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: IL-6 forward

<400> SEQUENCE: 10 tcctaccccca atttccaatg c                                                                              21

<210> SEQ ID NO 11
<211> LENGTH: 21
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: IL-6 reverse

<400> SEQUENCE: 11
tgaattggat ggtcttggtc c                                                                               21

<210> SEQ ID NO 12
<211> LENGTH: 34
<212> TYPE: DNA
<213> ORGANISM: Artificial sequence
<220> FEATURE:
<223> OTHER INFORMATION: sequence is synthesized
<220> FEATURE:
<221> NAME/KEY: PCR probe
<222> LOCATION: Full
<223> OTHER INFORMATION: IL-6 probe

<400> SEQUENCE: 12
aacagataag ctggagtcac agaaggagtg gcta                                                                 34

<210> SEQ ID NO 13
<211> LENGTH: 20
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: CTGF forward

<400> SEQUENCE: 13
ttggcccaga cccaactatg                                                                                 20

<210> SEQ ID NO 14
<211> LENGTH: 18
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: CTGF reverse

<400> SEQUENCE: 14
ggcgctccac tctgtggt                     18

<210> SEQ ID NO 15
<211> LENGTH: 21
<212> TYPE: DNA
<213> ORGANISM: Artificial sequence
<220> FEATURE:
<223> OTHER INFORMATION: sequence is synthesized
<220> FEATURE:
<221> NAME/KEY: PCR probe
<222> LOCATION: Full
<223> OTHER INFORMATION: CTGF probe

<400> SEQUENCE: 15
tgcgagccaa ctgcctggtc c                 21

<210> SEQ ID NO 16
<211> LENGTH: 22
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: TGF forward

<400> SEQUENCE: 16
accctggtgg tatactgaga ca                22

<210> SEQ ID NO 17
<211> LENGTH: 18
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: TGF reverse

<400> SEQUENCE: 17
ggggtctccc aaggaaag                     18

<210> SEQ ID NO 18
<211> LENGTH: 22
<212> TYPE: DNA
<213> ORGANISM: Artificial sequence
<220> FEATURE:
<223> OTHER INFORMATION: sequence is synthesized
<220> FEATURE:
<221> NAME/KEY: PCR probe
<222> LOCATION: Full
<223> OTHER INFORMATION: TGF probe

<400> SEQUENCE: 18
tgtcagagcc tcaccgcgac tc                22

<210> SEQ ID NO 19
<211> LENGTH: 20
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer -continued

```
<222> LOCATION: Full
<223> OTHER INFORMATION: aFGF forward

<400> SEQUENCE: 19
tgacgacttt tctggatgga                                                    20

<210> SEQ ID NO 20
<211> LENGTH: 22
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: aFGF reverse

<400> SEQUENCE: 20
acaaggaggc tactgagaaa gg                                                 22

<210> SEQ ID NO 21
<211> LENGTH: 27
<212> TYPE: DNA
<213> ORGANISM: Artificial sequence
<220> FEATURE:
<223> OTHER INFORMATION: sequence is synthesized
<220> FEATURE:
<221> NAME/KEY: PCR probe
<222> LOCATION: Full
<223> OTHER INFORMATION: aFGF probe

<400> SEQUENCE: 21
agtttccatt caccattagg agggagt                                            27

<210> SEQ ID NO 22
<211> LENGTH: 22
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: bFGF forward

<400> SEQUENCE: 22
cctctcagag acctacgttc aa                                                 22

<210> SEQ ID NO 23
<211> LENGTH: 18
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: bFGF reverse

<400> SEQUENCE: 23
ggaggtcaag gccacaat                                                      18

<210> SEQ ID NO 24
<211> LENGTH: 23
<212> TYPE: DNA
<213> ORGANISM: Artificial sequence
<220> FEATURE:
<223> OTHER INFORMATION: sequence is synthesized
<220> FEATURE:
```

<221> NAME/KEY: PCR probe
<222> LOCATION: Full
<223> OTHER INFORMATION: bFGF probe

<400> SEQUENCE: 24
cggtccaggt cttccaccaa ctg                                             23

<210> SEQ ID NO 25
<211> LENGTH: 18
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: PlGF forward

<400> SEQUENCE: 25
gcagtagccc gtggactt                                                   18

<210> SEQ ID NO 26
<211> LENGTH: 23
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: PlGF reverse

<400> SEQUENCE: 26
cggtccaggt cttccaccaa ctg                                             23

<210> SEQ ID NO 27
<211> LENGTH: 27
<212> TYPE: DNA
<213> ORGANISM: Artificial sequence
<220> FEATURE:
<223> OTHER INFORMATION: sequence is synthesized
<220> FEATURE:
<221> NAME/KEY: PCR probe
<222> LOCATION: Full
<223> OTHER INFORMATION: PlGF probe

<400> SEQUENCE: 27
acacacaacc cagacttgta tcggtca                                         27

<210> SEQ ID NO 28
<211> LENGTH: 20
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: Flt-1 forward

<400> SEQUENCE: 28
gtcaacggct gccctatgat                                                 20

<210> SEQ ID NO 29
<211> LENGTH: 20
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: Flt-1 reverse

<400> SEQUENCE: 29
ccgagcgatt tgcctagttt                                              20

<210> SEQ ID NO 30
<211> LENGTH: 25
<212> TYPE: DNA
<213> ORGANISM: Artificial sequence
<220> FEATURE:
<223> OTHER INFORMATION: sequence is synthesized
<220> FEATURE:
<221> NAME/KEY: PCR probe
<222> LOCATION: Full
<223> OTHER INFORMATION: Flt-1 probe

<400> SEQUENCE: 30
tctctcccgt gcaaactccc acttg                                        25

<210> SEQ ID NO 31
<211> LENGTH: 21
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: Flk-1 forward

<400> SEQUENCE: 31
tcattatcct cgtcggcact g                                            21

<210> SEQ ID NO 32
<211> LENGTH: 19
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: Flk-1 reverse

<400> SEQUENCE: 32
ccttcattgg cccgcttaa                                               19

<210> SEQ ID NO 33
<211> LENGTH: 30
<212> TYPE: DNA
<213> ORGANISM: Artificial sequence
<220> FEATURE:
<223> OTHER INFORMATION: sequence is synthesized
<220> FEATURE:
<221> NAME/KEY: PCR probe
<222> LOCATION: Full
<223> OTHER INFORMATION: Flk-1 probe

<400> SEQUENCE: 33
ttctggctcc ttcttgtcat tgtcctacgg                                   30

<210> SEQ ID NO 34
<211> LENGTH: 20
<212> TYPE: DNA
<213> ORGANISM: Artificial sequence
<220> FEATURE:

-continued

```
<223> OTHER INFORMATION: sequence is synthesized
<220> FEATURE:
<221> NAME/KEY: PCR primer
<222> LOCATION: Full
<223> OTHER INFORMATION: c-Met forward

<400> SEQUENCE: 34
gccctttcca gagacttgtt                                              20

<210> SEQ ID NO 35
<211> LENGTH: 20
<212> TYPE: DNA
<213> ORGANISM: Artificial sequence
<220> FEATURE:
<223> OTHER INFORMATION: sequence is synthesized
<220> FEATURE:
<221> NAME/KEY: PCR primer
<222> LOCATION: Full
<223> OTHER INFORMATION: c-Met reverse

<400> SEQUENCE: 35
catctcactg gcctgttctc                                              20

<210> SEQ ID NO 36
<211> LENGTH: 26
<212> TYPE: DNA
<213> ORGANISM: Artificial sequence
<220> FEATURE:
<223> OTHER INFORMATION: sequence is synthesized
<220> FEATURE:
<221> NAME/KEY: PCR probe
<222> LOCATION: Full
<223> OTHER INFORMATION: c-Met probe

<400> SEQUENCE: 36
cctatggact accactgcct agggga                                       26
```

COMPOSITIONS AND METHODS FOR LIVER GROWTH AND LIVER PROTECTION

This application is a continuation application of Ser. No. 10/455,470 filed on Jun. 5, 2003, which is a non-provisional application claiming priority to provisional application No. 60/386,637, filed Jun. 5, 2002, the entire disclosure of which is hereby incorporated by reference.

FIELD OF THE INVENTION

The present invention relates to the diagnostic and therapeutic uses of VEGFR modulating agents, including methods of utilizing VEGFR agonists for promoting liver growth, treating liver pathological conditions, and protecting liver from damage.

BACKGROUND OF THE INVENTION

Liver

The liver is the major metabolic control organ of the human body that comprises thousands of minute lobules (lobuli hepatis), the functional units of the organ. Liver tissue contains two major differentiated cell types: parenchymal cells (i.e., hepatocytes) and non-parenchymal cells. The complex functions of liver are exerted to a large extent by hepatocytes, whereas non-parenchymal cells such as Kupffer cells, Ito cells and liver sinusoidal endothelial cells (LSEC) play important roles in supporting and providing supplies to hepatocytes. Mochida et al. (1996) Biochem. Biophy. Res. Comm. 226:176-179.

The liver acts as a guardian interposed between the digestive tract and the rest of the body. A major hepatic function involves effective uptake, storage, metabolism and distribution to blood and bile large amounts of substances such as carbohydrates, lipids, amino acids, vitamins and trace elements. Another function of the liver is the detoxification of xenobiotic pollutants, drugs and endogenous metabolites, through both phase I (oxidation/reduction) and phase II (conjugation) mechanisms.

Because of its essential role to life, liver dysfunction and diseases are often debilitating and life threatening. A number of acute or chronic pathological conditions are associated with structural and/or functional abnormalities of the liver. These include, but are not limited to, liver failure, hepatitis (acute, chronic or alcohol), liver cirrhosis, toxic liver damage, medicamentary liver damage, hepatic encephalopathy, hepatic coma or hepatic necrosis.

Many chemical and biological agents, either therapeutic or purely harmful, can induce liver damages and thus are hepatotoxic. The susceptibility of the liver to damage by hepatotoxic agents may be related to its primary role in metabolism or is a consequence of hypersensitivity reactions. Up to 25% of cases of fulminant hepatic failure may be the result of adverse reactions to medical agents. Hepatotoxic compounds are also an important cause of chronic liver disease including fatty liver, hepatitis, cirrhosis and vascular and neoplastic lesions of the liver. (Sinclair et al., Textbook of Internal Medicine, 569-575 (1992) (editor, Kelley; Publisher, J. B. Lippincott Co.).

Hepatotoxic agents may induce liver damage by cytotoxicity to the liver directly or through the production of toxic metabolites (this category includes the hypersensitivity reaction which mimics a drug allergy); cholestasis, an arrest in the flow of bile due to obstruction of the bile ducts; and vascular lesions, such as in veno occlusive disease (VOD), where injury to the vascular endothelium results in hepatic vein thrombosis. Individual susceptibility to liver damage induced by hepatotoxic agents is influenced by genetic factors, age, sex, nutritional status, exposure to other drugs, and systemic diseases (Sinclair et al., Textbook of Internal Medicine, Supra).

In addition to normal growth during early development, liver tissue has a unique ability to regenerate at adult stage. Liver regeneration after the loss of hepatic tissue is a fundamental component of the recovery process in response to various forms of liver injury such as hepatotoxicity, viral infection, vascular injury and partial hepatectomy. Following partial hepatectomy, for example, the liver size is usually restored to its original mass within about six days. Liver growth and regeneration involves proliferation of both hepatocytes and non-parenchymal cells such as sinusoidal endothelial cells. Typically, hepatocytes are the first to proliferate, and other cells of the liver enter into DNA synthesis about 24 hours after the hepatocytes. Michalopoulos and DeFrances (1997) Science 276:60-65.

Factors for Liver Proliferation

Several growth factors and cytokines have been implicated as being able to induce liver regeneration, most notably hepatocyte growth factor (HGF), epidermal growth factor (EGF), transforming growth factor-α (TGF-α), interleukin-6 (IL-6), tumor necrosis factor-α (TNF-α), basic and acidic fibroblast growth factors, CTGF, HB-EGF, and norepinephrine. Fujiwara et al. (1993) Hepatol. 18:1443-9; Baruch et al. (1995) J. Hepatol. 23:328-32; Ito et al. (1994) Biochem. Biophys. Res. Commun. 198:25-31; Suzuma et al. (2000) J. Biol. Chem. 275:40725-31; Michalopoulos and DeFrances (1997) supra. As one of the most potent liver mitogens, HGF was first identified as a factor capable of stimulating DNA synthesis in cultured hepatocytes but is now known to have multiple distinct functions on a variety of epithelial cells. Nakamura et al. (1984) Biochem. Biophys. Res. Comm. 122:1450; Russell et al. (1984) J. Cell. Physiol. 119:183-192. Scatter factor (SF), which enhances motility and invasiveness of certain cell types, was found to have identical amino acid sequence as HGF, leading to the designation HGF/SF. Stoker and Perryman (1985) J. Cell Sci. 77:209-223; Gherardi and Stoker (1990) Nature 346:228. HGF/SF is synthesized as an inactive, single-chain zymogen that is subsequently cleaved to produce an active, dimeric glycoprotein composed of a 69-kDa α-subunit and a 34-kDa β-subunit held together by a single disulfide bond. Nakamura et al. (1989) Nature 342:440-443; Roos et al. (1995) Am. J. Physiol. 268:G380-6.

All known biological effects of HGF are transduced via a single tyrosine kinase receptor, Met, the product of the Met protooncogene. HGF/SF acts predominantly on Met-expressing epithelial cells in an endocrine and/or paracrine fashion, to mediate such diverse biological activities as proliferation, branching, cell migration, morphogenesis and lumen formation. van der Voort et al. Adv. Cancer Res. 79:39-90 (2000). In the liver, HGF is expressed in non-hepatocyte cells such as Ito cells and LSECs, whereas met transcripts are strongly expressed in hepatocytes. Hu et al. Am. J. Pathol. 142:1823-1830 (1993). After chemical or mechanical liver injury, HGF levels sharply increase, leading to a strong hepatocyte proliferation. Horimoto et al. J. Hepatol. 23:174-183 (1995). Livers from transgenic mice with liver-specific overexpression of HGF are twice the size of livers of control animals and they regenerate much faster after partial hepatectomy. Sakata et al. (1996) Cell Growth Differ. 7:1513-1523; Shiota et al. (1994) Hepatol. 19:962-972. Furthermore, HGF null mutant mouse embryos fail to develop a fully functional liver, demonstrating the essential role of HGF during liver development. Schmidt et al. (1995) *Nature* 373:699-702. The continuous infusion of large doses (5 mg/kg/day) of HGF directly into the portal vein has been shown to result in a significant increase of relative liver mass in mice. Patijn et al. (1998) *Hepatol.* 28:707-16. While HGF was found to be a potent inducer of hepatocyte mitosis, however, it failed to induce proliferation of non-parenchymal cells including sinusoidal endothelial cells. Patijn et al., supra. In other biological contexts, conversely, HGF has been shown as a potent endothelial cell mitogen. Rosen and Goldberg (1997) In: Regulation of Angiogenesis. Rosen, E, Goldberg, ID, Eds. Springer Verlag. pp 193-208.

It has been suggested that substantially high HGF plasma concentrations may be required in order to promote liver growth in vivo (Roos et al. (1995) *Am. J. Physiol.* 268:G380-6). HGF, by virtue of its strong heparin-binding properties, is largely sequestered in extrahepatic tissues following intravenous administration (Zioncheck et al. (1994) *Endocrinology* 134:1879-87) and the co-administration of dextran sulfate is required for an effective liver-promoting action (Roos et al., 1995).

Angiogenesis and Liver

Angiogenesis is an important cellular event in which vascular endothelial cells proliferate, prune and reorganize to form new vessels from preexisting vascular network. There are compelling evidences that the development of a vascular supply is essential for normal and pathological proliferative processes (Folkman and Klagsbrun (1987) *Science* 235:442-447). Delivery of oxygen and nutrients, as well as the removal of catabolic products, represent rate-limiting steps in the majority of growth processes occurring in multicellular organisms. Thus, it has been generally assumed that the vascular compartment is necessary, albeit but not sufficient, not only for organ development and differentiation during embryogenesis, but also for wound healing and reproductive functions in the adult. However, recent evidence suggests that, at least in the mouse embryo, the vascular endothelium may have an inductive effect on liver (Matsumoto et al. (2001) *Science* 294:559-563) and pancreas organogenesis (Lammert et al. (2001) *Science* 294:564-567), even prior to the establishment of a blood flow. The mechanism of such induction is unknown.

Angiogenesis is also implicated in the pathogenesis of a variety of disorders, including but not limited to, proliferative retinopathies, age-related macular degeneration, tumors, rheumatoid arthritis (RA), and psoriasis. Folkman (1995) *Nat Med* 1:27-31. Regenerating liver, in analogy to rapidly growing tumors, must synthesize new stroma and blood vessels. Not surprisingly, therefore, many studies have focused on angiogenesis in liver development and regeneration, as well as the roles of many known angiogenic factors therein. Michalopoulos and DeFrances (1997) supra; Mochida et al. (1996).

Vascular endothelial cell growth factor (VEGF), a potent mitogen for vascular endothelial cells, has been reported as a key regulator of angiogenesis and vasculogenesis. Ferrara and Davis-Smyth (1997)*Endocrine Rev.* 18:4-25; Ferrara (1999) J. Mol. Med. 77:527-543. Compared to other growth factors that contribute to the processes of vascular formation, VEGF is unique in its high specificity for endothelial cells within the vascular system. Recent evidence indicates that VEGF is essential for embryonic vasculogenesis and angiogenesis. Carmeliet et al. (1996) *Nature* 380:435-439; Ferrara et al. (1996) *Nature* 380:439-442. Furthermore, VEGF is required for the cyclical blood vessel proliferation in the female reproductive tract and for bone growth and cartilage formation. Ferrara et al. (1998) *Nature Med.* 4:336-340; Gerber et al. (1999) *Nature* Med. 5:623-628.

In addition to being an angiogenic factor in angiogenesis and vasculogenesis, VEGF, as a pleiotropic growth factor, exhibits multiple biological effects in other physiological processes, such as endothelial cell survival, vessel permeability and vasodilation, monocyte chemotaxis and calcium influx. Ferrara and Davis-Smyth (1997), supra. Moreover, recent studies have reported mitogenic effects of VEGF on a few non-endothelial cell types, such as retinal pigment epithelial cells, pancreatic duct cells and Schwann cells. Guerrin et al. (1995) J. Cell Physiol. 164:385-394; Oberg-Welsh et al. (1997) Mol. Cell. Endocrinol. 126:125-132; Sondell et al. (1999) J. Neurosci. 19:5731-5740.

Substantial evidence also implicates VEGF's critical role in the development of conditions or diseases that involve pathological angiogenesis. The VEGF mRNA is overexpressed by the majority of human tumors examined (Berkman et al. *J Clin Invest* 91:153-159 (1993); Brown et al. *Human Pathol.* 26:86-91 (1995); Brown et al. *Cancer Res.* 53:4727-4735 (1993); Mattern et al. *Brit. J. Cancer.* 73:931-934 (1996); and Dvorak et al. *Am J. Pathol.* 146:1029-1039 (1995)). Also, the concentration of VEGF in eye fluids are highly correlated to the presence of active proliferation of blood vessels in patients with diabetic and other ischemia-related retinopathies (Aiello et al. *N. Engl. J. Med.* 331:1480-1487 (1994)). Furthermore, recent studies have demonstrated the localization of VEGF in choroidal neovascular membranes in patients affected by AMD (Lopez et al. *Invest. Ophtalmo. Vis. Sci.* 37:855-868 (1996)). Anti-VEGF neutralizing antibodies suppress the growth of a variety of human tumor cell lines in nude mice (Kim et al. *Nature* 362:841-844 (1993); Warren et al. *J. Clin. Invest.* 95:1789-1797 (1995); Borgström et al. *Cancer Res.* 56:4032-4039 (1996); and Melnyk et al. *Cancer Res.* 56:921-924 (1996)) and also inhibit intraocular angiogenesis in models of ischemic retinal disorders (Adamis et al. *Arch. Ophthalmol.* 114:66-71 (1996)). Therefore, anti-VEGF monoclonal antibodies or other inhibitors of VEGF action are promising candidates for the treatment of solid tumors and various intraocular neovascular disorders.

Human VEGF was obtained by first screening a cDNA library prepared from human cells, using bovine VEGF cDNA as a hybridization probe. Leung et al. (1989) *Science,* 246:1306. One cDNA identified thereby encodes a 165-amino acid protein having greater than 95% homology to bovine VEGF; this 165-amino acid protein is typically referred to as human VEGF (hVEGF) or $VEGF_{165}$. The mitogenic activity of human VEGF was confirmed by expressing the human VEGF cDNA in mammalian host cells. Media conditioned by cells transfected with the human VEGF cDNA promoted the proliferation of capillary endothelial cells, whereas control cells did not. Leung et al. (1989) *Science,* supra.

Although a vascular endothelial cell growth factor could be isolated and purified from natural sources for subsequent therapeutic use, the relatively low concentrations of the protein in follicular cells and the high cost, both in terms of effort and expense, of recovering VEGF proved commercially unavailing. Accordingly, further efforts were undertaken to clone and express VEGF via recombinant DNA techniques. (See, e.g., Ferrara (1995) *Laboratory Investigation* 72:615-618 (1995), and the references cited therein).

VEGF is expressed in a variety of tissues as multiple homodimeric forms (121, 145, 165, 189, and 206 amino acids per monomer) resulting from alternative RNA splicing. $VEGF_{121}$ is a soluble mitogen that does not bind heparin; the longer forms of VEGF bind heparin with progressively higher affinity. The heparin-binding forms of VEGF can be cleaved in the carboxy terminus by plasmin to release a diffusible form(s) of VEGF. Amino acid sequencing of the carboxy terminal peptide identified after plasmin cleavage is $Arg_{110}$-$Ala_{111}$. Amino terminal "core" protein, VEGF (1-110) isolated as a homodimer, binds neutralizing monoclonal antibodies (such as the antibodies referred to as 4.6.1 and 3.2E3.1.1) and soluble forms of VEGF receptors with similar affinity compared to the intact $VEGF_{165}$ homodimer.

Several molecules structurally related to VEGF have also been identified recently, including placenta growth factor (PIGF), VEGF-B, VEGF-C, VEGF-D and VEGF-E. Ferrara and Davis-Smyth (1987) Endocr. Rev., supra; Ogawa et al. (1998) J. Biological Chem. 273:31273-31281; Meyer et al. (1999) EMBO J., 18:363-374. A receptor tyrosine kinase, Flt-4 (VEGFR-3), has been identified as the receptor for VEGF-C and VEGF-D. Joukov et al. (1996) EMBO. J. 15:1751; Lee et al. (1996) Proc. Natl. Acad. Sci. USA 93:1988-1992; Achen et al. (1998) Proc. Natl. Acad. Sci. USA 95:548-553. VEGF-C has recently been shown to be involved in the regulation of lymphatic angiogenesis. Jeltsch et al. (1997) Science 276:1423-1425.

Two VEGF receptors have been identified, Flt-1 (also called VEGFR-1) and KDR (also called VEGFR-2). Shibuya et al. (1990) Oncogene 8:519-527; de Vries et al. (1992) Science 255:989-991; Terman et al. (1992) Biochem. Biophys. Res. Commun. 187:1579-1586. Neuropilin-1 has been shown to be a selective VEGF receptor, able to bind the heparin-binding VEGF isoforms (Soker et al. (1998) Cell 92:735-45). Both Flt-I and KDR belong to the family of receptor tyrosine kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, Ann. Rev. Biochem. 57:433-478, 1988; Ullrich and Schlessinger, Cell 61:243-254, 1990). The intrinsic function of RTKs is activated upon ligand binding, which results in phosphorylation of the receptor and multiple cellular substrates, and subsequently in a variety of cellular responses (Ullrich & Schlessinger, 1990, Cell 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see, Schlessinger and Ullrich, 1992, Neuron 9:1-20. Structurally, both Flt-1 and KDR have seven immunoglobulin-like domains in the extracellular domain, a single transmembrane region, and a consensus tyrosine kinase sequence which is interrupted by a kinase-insert domain. Matthews et al. (1991) Proc. Natl. Acad. Sci. USA 88:9026-9030; Terman et al. (1991) Oncogene 6:1677-1683.

There are compelling evidences suggesting that Flt-1 and KDR have different signal transduction properties and possibly mediate different functions. Moreover, the signals mediated through Flt-1 and KDR appear to be cell type specific. Recent studies have provided considerable experimental data indicating that KDR is the major mediator of the mitogenic, angiogenic and permeability-enhancing effects of VEGF (Ferrara (1999) Kidney Int. 56:794-814). VEGF stimulation leads to a robust auto-phosphorylation of KDR and activation of the MAPK cascade, which may directly contribute to endothelial cell proliferation (Kroll and Waltenberger (1997) J. Biol. Chem. 272:32521-7). In contrast, the function of VEGFR-1 has been less clear, and many apparently conflicting reports on its function exist in the literature. This molecule displays a very weak or undetectable tyrosine autophosphorylation in endothelial cells in response to VEGF (Gille et al. (2000) EMBO J. 19:4064-4073). Flt-1 has been shown to have inhibitory effects on endothelial mitogenesis in several biological contexts, including early embryonic development, either by acting as a "decoy" receptor that prevents VEGF binding to VEGFR-2 or by directly inhibiting VEGFR-2 activities. Park et al. (1994) J. Biol. Chem. 269:25646-54; U.S. Pat. No. 6,107,046 (Alitalo et al.); Fong et al. (1999) Development 126:3015-25; Zeng et al. (2001). J. Biol. Chem. 276:26969-79). Other studies suggest that VEGFR-1 may mediate recruitment of monocytes and endothelial cell progenitors to the tumor vasculature (Barleon et al. (1996) Blood 87:3336-43) (Lyden et al. (2001) Nat. Med. 7:1194-201). Thus, the importance of VEGFR-1 signaling in the vascular endothelium is largely unclear.

Recent studies have attempted to elucidate the molecular mechanisms of various physiological and pathological processes in the liver, particularly liver regeneration. There have been proposed two reciprocal paracrine communication systems existing in hepatic tissues between hepatocytes and non-parenchymal cells such as sinusoidal endothelial cells. In one direction, growth factors such as HGF/SF are released from non-parenchymal cells such as sinusoidal endothelial cells and Kupfer cells, bind to their receptors (such as the c-Met receptor) on hepatocytes, and in turn induce and promote hepatocyte proliferation. In the opposite direction, it is suggested that VEGF expressed in and secreted from hepatocytes acts as a stimulatory factor that binds to its receptors (KDR and Flt-1) on sinusoidal endothelial cells, thereby stimulating the proliferation and maintenance of the sinusoidal endothelial cells in the liver. Yamane et al. (1994) Oncogene 9:2683-2690 observed that the endogenous expression of VEGF and VEGF receptors (Flt and KDR) as well as HGF and c-Met are strictly regulated in a cell-type specific manner in liver: using a flt-1 cDNA as a probe, flt-1 mRNA was found to be expressed at very high levels in sinusoidal endothelial cells in normal rat liver, but was hardly detectable in hepatocytes. Similar expression pattern was found for KDR, although the expression level was much lower. Yamane et al. further observed that, in an in vitro cell culture system, VEGF demonstrated a remarkably specific growth-stimulatory activity as well as maintenance activity on the sinusoidal endothelial cells.

Mochida et al. (1996) Biochem. Biophy. Res. Comm. 226:176-179 conducted in vitro experiments to monitor the expression levels of VEGF and VEGFRs in isolated hepatic cells from normal livers or partially resected livers. They found that in 70% resected rat liver, expression of VEGF, Flt-1 and KDR were all significantly increased. And the timing of the expression peaks for Flt-1 and KDR suggested that the upregulation of VEGFRs may be involved in proliferation of sinusoidal endothelial cells during liver regeneration.

More recently, Ajioka et al. (1999) Hepatology 29:396-402 examined the fate of transplanted hepatic tissues in the presence of exogenous VEGF. Isolated hepatocytes of adult mice were transfected with VEGF gene in vitro then transplanted intraperitoneally (i.p.) in mice, into an area adjacent to the pancreas. The transplanted hepatocytes formed a large number of tissue aggregates in vivo. In vitro staining showed that these VEGF-transfected tissues underwent substantial proliferation and developed a significant vascular network therein. Thus, the results suggested that the expression of VEGF conferred the formation of a vascular network, which in turn may promoted tissue formation. The results, however, showed absence of any nonparenchymal cells or growth factors derived from them in the VEGF-transfected, transplanted hepatic tissues.

Assy et al. (1999) *J. Hepatol.* 30:911-915 studied the effect of VEGF as an angiogenic factor in liver regeneration following partial hepatectomy in rat. Rats undergoing 30% partial hepatectomy were administered intravenously (i.v.) VEGF and sacrificed at 24, 36 and 48 hour postoperatively. Whilst the study showed increased DNA synthesis activities of hepatocytes in the VEGF-treated rats at 36 and 48 h after PHx, and suggested that stimulation of neovascularization by VEGF is important during liver regeneration, no statistically significant changes in restituted liver mass were observed in VEGF-treated rats as compared to control rats without VEGF treatment.

SUMMARY OF THE INVENTION

The present invention provides methods for promoting liver growth in a subject, comprising administering to the subject an effective amount of a VEGFR modulating agent. The VEGFR modulating agent useful for the present invention can be an agonist specific to one of the VEGF receptors such as a Flt-1 agonist. Preferably, the Flt-1 agonist can be a Flt-1 selective VEGF variant (Flt-sel) that selectively binds to Flt-1, a growth factor that binds and activates Flt-1 such as PIGF or VEGF-B, an anti-Flt-1 agonistic antibody or a small molecule agonist. In a preferred embodiment, the Flt-1 agonist is administered in combination with an angiogenic agent such as VEGF or a KDR selective variant thereof.

In another aspect, the present invention provides methods for treating a pathological liver condition in a subject, comprising administering to the subject a VEGFR modulating agent in a manner effective to alleviate the pathological liver condition. Pathological liver conditions that can be treated by the present invention include, but not limited to, liver failure, hepatitis, liver cirrhosis, toxic liver damage, medicamentary liver damage, hepatic encephalopathy, hepatic coma or hepatic necrosis. Preferably, the VEGFR modulating agent comprises a Flt-1 agonist, optionally in combination with an angiogenic agent.

Also provided in the present invention are methods for protecting liver in a subject from damage due to exposure to a hepatotoxic agent, comprising administering to the subject a VEGFR modulating agent, wherein said VEGFR modulating agent effectively protects liver from damage. Preferably, the VEGFR modulating agent comprises a Flt-1 agonist, optionally in combination with an angiogenesis agent. In one aspect, the VEGFR modulating agent is administered prior to or concurrent with the exposure of said subject to the hepatotoxic agent, said hepatotoxic agent being a therapeutic agent such as a chemotherapeutic or radiation agent for treating cancers. As such, the methods serve to enhance the efficacy of the treatment by permitting the subject tolerance to high doses of the therapeutic agents. In another aspect, the VEGFR modulating agent is administered after the exposure of the subject to a hepatotoxic agent but prior to any detectable liver damage in the subject. Such methods are especially useful for treating liver damages due to accidental exposure of the subject to a hepatotoxic agent.

In various methods of the present invention, the subject agents can be administered to the subject through a systemic delivery system, such as a cell preparation comprising mammalian cells (e.g., CHO cells) expressing a recombinant form of the subject agent. The systemic delivery system can comprise a slow release preparation comprising purified agent and a polymer matrix. Alternatively, the subject agent of the invention can be administered via a liver-targeted gene delivery vector comprising a nucleic acid encoding the agent. Well established viral or nonviral vectors for gene therapy can be used as the liver-targeted gene delivery vector in the present invention.

An article of manufacture and a kit comprising a VEGFR modulating agent are also provided.

DETAILED DESCRIPTION OF THE PREFERRED EMBODIMENTS

General

Figure 1B:
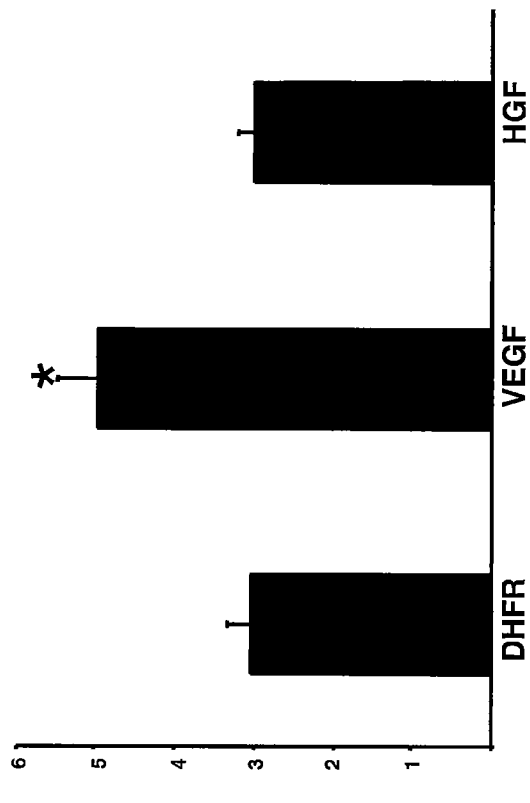
FIGS. 1A-1D show effects of systemic VEGF on liver mass increases. 1A and 1B compare liver/brain ratios in animals implanted with CHO cells expressing DHFR, $VEGF_{165}$, HGF or HAg (Hakata antigen). 1C: Kidney/brain ratios in animals implanted with DHFR, $VEGF_{165}$ or HGF-expressing CHO cells. 1D: Brain weights of the same groups as 1C. Error bars represent standard error of the mean.

The present invention provides, for the first time, a concerted system in which systemically delivered VEGFR modulating agents act in a paracrine fashion to promote liver growth. Not wishing to be bound by particular mechanisms of action, the current system may create a local cascade of signaling events originating in sinusoidal endothelial cells following VEGF receptor activation, which is much more potent and beneficial in promoting hepatocyte proliferation and liver growth than systemic delivery of the principal liver mitogen, HGF. The vasculature has been long thought to be necessary, but not sufficient, for proliferative processes, through the delivery of nutrients and oxygen and removal of catabolic products. The present invention demonstrates that, following an appropriate instructive signal, the vascular endothelium can be sufficient to initiate and amplify a growth/survival process that may overcome the set point for final organ size and protect the parenchyma from injury.

Particularly enticing are the surprising findings on a novel function of the VEGFR-1 (Flt-1) RTK in regulating key paracrine activities of LSEC, which in turn leads to liver proliferation and protection. Strikingly, in spite of the lack of stimulation of angiogenesis, activation of VEGFR-1 was sufficient to substantially protect the liver parenchyma from toxic injury. Indeed, the present invention provides the first evidence that protective effects on parenchymal cells mediated by the endothelium can be uncoupled from stimulation of angiogenesis.

Given that the known dose-limiting effects of VEGF (e.g. hypotension, edema) (Yang et al. (1998) *J. Pharmacol. Exp. Ther.* 284:103-10) are associated with KDR activation (Kliche and Waltenberger (2001) *IUBMB Life* 52:61-6), it is contemplated that a Flt-1 agonist, such as a Flt-selective VEGF variant, can form the basis of a therapeutic scheme aimed toward liver protection. The addition of a KDR agonist or other angiogenic factor at a lower ratio may result in a maximal therapeutic benefit, by providing stimulation of angiogenesis. Alternatively, a VEGF variant that preferentially activates Flt-1 versus KDR might combine optimal characteristics of safety and efficacy. The potential indications include acute liver damage induced by various drugs, chemotherapy, or toxins as well as chronic injury, including cirrhosis.

Compositions of the Invention and Their Productions

The present invention relates to uses of various agents capable of modulating VEGFR activities in the liver. The term "VEGF receptor" or "VEGFR" as used herein refers to a cellular receptor for VEGF, ordinarily a cell-surface receptor found on vascular endothelial cells, as well as fragments and variants thereof which retain the ability to bind VEGF (such as fragments or truncated forms of the extracellular domain). Some examples of VEGFR include the protein kinase receptors referred to in the literature as Flt-1 and KDR/Flk-1.

DeVries et al. *Science*, 255:989 (1992); Shibuya et al. *Oncogene*, 5:519 (1990); Matthews et al. *Proc. Nat. Acad. Sci.*, 88:9026 (1991); Terman et al. *Oncogene*, 6:1677 (1991); and Terman et al. *Biochem. Biophys. Res. Commun.*, 187:1579 (1992). The Flt-1 (fms-like-tyrosine kinase) and KDR (kinase domain region) receptors bind VEGF with high affinity. Flk-1 (fetal liver kinase-1), the murine homolog of KDR, shares 85% sequence identity with human KDR. Ferrara (1999) *Kidney Intl.* 56:794-814. Both Flt-1 and KDR/Flk-1 have seven immunoglobulin (Ig)-like domains in the extracellular domain (ECD), a single transmembrane region and a consensus tyrosine kinase (TK) sequence, which is interrupted by a kinase-insert domain. Flt-1 has the highest affinity for rhVEGF$_{165}$, with a Kd of approximately 10 to 20 pM. KDR has a lower affinity for VEGF, with a Kd of approximately 75 to 125 pM.

Other VEGF receptors include those that can be cross-link labeled with VEGF, or that can be co-immunoprecipitated with KDR or Flt-1. An additional VEGF receptor that binds VEGF$_{165}$ but not VEGF$_{12}$, has been identified. Soker et al (1998) *Cell* 92:735-45. The isoform-specific VEGF binding site is identical to human neuropilin-1, a receptor for the collapsin/semaphorin family that mediates neuronal cell guidance.

The Flt-1 and KDR receptors mainly exist as a bound receptor on the surface of vascular endothelial cells, although they can also be present in non-endothelial cells. Some soluble forms of VEGFR have also been found. For example, a cDNA coding an alternatively spliced soluble form of Flt-1 (sFlt-1), lacking the seventh Ig-like domain, transmembrane sequence, and the cytoplasmic domain, has been identified in human umbilical vein endothelial cells (HUVECs). Kendall et al. (1996) *Biochem. Biophys. Res. Comm.* 226:324-328.

The term "agent" or, alternatively, "compound" as used herein refers broadly to any substance with identifiable molecular structure and physiochemical property. Non-limiting examples of agents capable of modulating VEGFR activities include antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like.

The VEGFR modulating agents encompassed by the invention can be either an agonist or an antagonist of a VEGFR. An "agonist" is an agent that mediates or activate the biological activity of its target. For example, a VEGFR agonist can be a growth factor ligand or an antibody that binds to the VEGFR's extracellular domain and triggers its signal transduction activity. Alternatively, a VEGFR agonist can be a small molecule compound that binds to the VEGFR's cytoplasmic domain and mediates its tyrosine phosphorylation. An "antagonist", on the other hand, is one which blocks, inhibits or reduces biological activity of its target. Such inhibition can occur by any means, e.g. by interfering with: ligand binding to the receptor, receptor complex formation, tyrosine kinase activity of a tyrosine kinase receptor in a receptor complex and/or phosphorylation of tyrosine kinase residue(s) in or by the receptor.

In a preferred embodiment, the agonist or antagonist of the invention is "selective" or "specific" to Flt-1, i.e., it exclusively or preferably modulates Flt-1 over other receptor tyrosine kinases such as KDR. In another embodiment, the agonist or antagonist of the invention is "selective" or "specific" to KDR, i.e., it exclusively or preferably modulates KDR over other receptor tyrosine kinases such as Flt-1.

In one aspect, the VEGFR agonist of the invention comprises a VEGF variant polypeptide capable of selectively binding to Flt-1 (referred hereinafter as "Flt-1 selective VEGF variant", or "Flt-sel", or "Flt$^{sel}$"). The term "VEGF" as used herein refers to the 165-amino acid vascular endothelial cell growth factor and related 121-, 189-, and 206-amino acid vascular endothelial cell growth factors, as described by Leung et al. *Science,* 246:1306 (1989), and Houck et al. *Mol. Endocrin.,* 5:1806 (1991), together with the naturally occurring allelic and processed forms thereof. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

The term "VEGF variant" as used herein refers to a VEGF polypeptide which includes one or more amino acid mutations in the native VEGF sequence. Optionally, the one or more amino acid mutations include amino acid substitution (s). For purposes of shorthand designation of VEGF variants described herein, it is noted that numbers refer to the amino acid residue position along the amino acid sequence of the putative native VEGF (provided in Leung et al., supra and Houck et al., supra.).

VEGF and variants thereof for use in the present invention can be prepared by a variety of methods well known in the art. Preferably, the VEGF employed in the methods of the present invention comprises recombinant VEGF$_{165}$. Amino acid sequence variants of VEGF can be prepared by mutations in the VEGF DNA. Such variants include, for example, deletions from, insertions into or substitutions of residues within the amino acid sequence shown in Leung et al., supra and Houck et al., supra. Any combination of deletion, insertion, and substitution may be made to arrive at the final construct having the desired activity. Obviously, the mutations that will be made in the DNA encoding the variant must not place the sequence out of reading frame and preferably will not create complementary regions that could produce secondary mRNA structure. EP 75,444A.

The VEGF variants optionally are prepared by site-directed mutagenesis of nucleotides in the DNA encoding the native VEGF or phage display techniques, thereby producing DNA encoding the variant, and thereafter expressing the DNA in recombinant cell culture.

While the site for introducing an amino acid sequence variation is predetermined, the mutation per se need not be predetermined. For example, to optimize the performance of a mutation at a given site, random mutagenesis may be conducted at the target codon or region and the expressed VEGF variants screened for the optimal combination of desired activity. Techniques for making substitution mutations at predetermined sites in DNA having a known sequence are well-known, such as, for example, site-specific mutagenesis.

Preparation of the VEGF variants described herein is preferably achieved by phage display techniques, such as those described in the PCT publication WO 00/63380.

After such a clone is selected, the mutated protein region may be removed and placed in an appropriate vector for protein production, generally an expression vector of the type that may be employed for transformation of an appropriate host.

Amino acid sequence deletions generally range from about 1 to 30 residues, more preferably 1 to 10 residues, and typically are contiguous.

Amino acid sequence insertions include amino- and/or carboxyl-terminal fusions of from one residue to polypeptides of essentially unrestricted length as well as intrasequence insertions of single or multiple amino acid residues. Intrasequence insertions (i.e., insertions within the native VEGF sequence) may range generally from about 1 to 10 residues, more preferably 1 to 5. An example of a terminal insertion includes a fusion of a signal sequence, whether heterologous or homologous to the host cell, to the N-terminus to facilitate the secretion from recombinant hosts.

Additional VEGF variants are those in which at least one amino acid residue in the native VEGF has been removed and a different residue inserted in its place. Such substitutions may be made in accordance with those shown in Table 1.

TABLE 1

| Original Residue | Exemplary Substitutions |
|---|---|
| Ala (A) | gly; ser |
| Arg (R) | lys |
| Asn (N) | gln; his |
| Asp (D) | glu |
| Cys (C) | ser |
| Gln (Q) | asn |
| Glu (E) | asp |
| Gly (G) | ala; pro |
| His (H) | asn; gln |
| Ile (I) | leu; val |
| Leu (L) | ile; val |
| Lys (K) | arg; gln; glu |
| Met (M) | leu; tyr; ile |
| Phe (F) | met; leu; tyr |
| Ser (S) | thr |
| Thr (T) | ser |
| Trp (W) | tyr |
| Tyr (Y) | trp; phe |
| Val (V) | ile; leu |

Changes in function or immunological identity may be made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in the VEGF variant properties will be those in which (a) glycine and/or proline (P) is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; (e) a residue having an electronegative side chain is substituted for (or by) a residue having an electropositive charge; or (f) a residue having a bulky side chain, e.g., phenylalanine, is substituted for (or by) one not having such a side chain, e.g., glycine.

The effect of the substitution, deletion, or insertion may be evaluated readily by one skilled in the art using routine screening assays. For example, a phage display-selected VEGF variant may be expressed in recombinant cell culture, and, optionally, purified from the cell culture. The VEGF variant may then be evaluated for KDR or Flt-1 receptor binding affinity and other biological activities, such as those disclosed in the present application. The binding properties or activities of the cell lysate or purified VEGF variant can be screened in a suitable screening assay for a desirable characteristic. For example, a change in the immunological character of the VEGF variant as compared to native VEGF, such as affinity for a given antibody, may be desirable. Such a change may be measured by a competitive-type immunoassay, which can be conducted in accordance with techniques known in the art. The respective receptor binding affinity of the VEGF variant may be determined by ELISA, RIA, and/or BIAcore assays, known in the art and described further in the Examples below. Preferred VEGF variants of the invention will also exhibit activity in KIRA assays (such as described in the Examples) reflective of the capability to induce phosphorylation of the KDR receptor. Preferred VEGF variants of the invention will additionally or alternatively induce endothelial cell proliferation (which can be determined by known art methods such as the HUVEC proliferation assay in the Examples). In addition to the specific VEGF variants disclosed herein, the VEGF variants described in Keyt et al. (1996) *J. Biol. Chem.* 271:5638-5646 are also contemplated for use in the present invention.

Flt-sel and methods of making the same have been known and are described in the Example sections below. Additional disclosures relating to Flt-sel can be found in, for example, the PCT publication WO 00/63380 and Li et al. (2000) *J. Biol. Chem.* 275:29823-29828. Preferred Flt-sel variants include one or more amino acid mutations and exhibit binding affinity to the Flt-1 receptor which is equal to or greater ($\geqq$) than the binding affinity of native VEGF to the Flt-1 receptor, and even more preferably, such VEGF variants exhibit less binding affinity ($<$) to the KDR receptor than the binding affinity exhibited by native VEGF to KDR. When binding affinity of such VEGF variant to the Flt-1 receptor is approximately equal (unchanged) or greater than (increased) as compared to native VEGF, and the binding affinity of the VEGF variant to the KDR receptor is less than or nearly eliminated as compared to native VEGF, the binding affinity of the VEGF variant, for purposes herein, is considered "selective" for the Flt-1 receptor. Preferred Flt-1 selective VEGF variants of the invention will have at least 10-fold less binding affinity to KDR receptor (as compared to native VEGF), and even more preferably, will have at least 100-fold less binding affinity to KDR receptor (as compared to native VEGF). The respective binding affinity of the VEGF variant may be determined by ELISA, RIA, and/or BIAcore assays, known in the art and described in the PCT publication WO 00/63380.

In some aspects of the invention, various methods for liver treatment further comprise administering an agent capable of modulating KDR activities. For example, a KDR agonist can be administered in combination with a Flt-1 agonist to promote liver growth or liver regeneration. KDR has been identified as the major receptor tyrosine kinase that mediates VEGF's activities in endothelial cell proliferation. Thus, agonists of KDR and Flt-1 will induce concerted proliferation of both the SECs and hepatocytes, thereby promoting a coordinated growth of liver.

In one aspect, the KDR agonist comprises a VEGF variant polypeptide capable of selectively binding to KDR (referred hereinafter as "KDR selective VEGF variant", or "KDR-sel", or "KDR$^{sel}$"). KDR-sel VEGF variants and methods of making the same are described in detail in the Example sections below. Additional disclosures relating to KDR-sel can be found in, for example, the PCT publication WO 00/63380 and Li et al. (2000) *J. Biol. Chem.* 275:29823-29828. Preferred KDR-sel include one or more amino acid mutations and exhibit binding affinity to the KDR receptor which is equal to or greater ($\geqq$) than the binding affinity of native VEGF to the KDR receptor, and even more preferably, the VEGF variants exhibit less binding affinity ($<$) to the flt-1 receptor than the binding affinity exhibited by native VEGF to Flt-1. When binding affinity of such VEGF variant to the KDR receptor is approximately equal (unchanged) or greater than (increased) as compared to native VEGF, and the binding affinity of the VEGF variant to the flt-1 receptor is less than or nearly eliminated as compared to native VEGF, the binding affinity of the VEGF variant, for purposes herein, is considered "selective" for the KDR receptor. Preferred KDR-sel of the invention will have at least 10-fold less binding affinity to Flt-1 receptor (as compared to native VEGF), and even more preferably, will have at least 100-fold less binding affinity to Flt-1 receptor (as compared to native VEGF). The respective binding affinity of the VEGF variant may be determined by ELISA, RIA, and/or BIAcore assays that are known in the art. Preferred KDR-sel of the invention will also exhibit activity in KIRA assays reflective of the capability to induce phosphorylation of the KDR receptor. Preferred KDR selective VEGF variants of the invention will additionally or alternatively induce endothelial cell proliferation (which can be determined by known methods such as the HUVEC proliferation assay).

In one aspect, the VEGFR modulating agents of the invention, such as VEGF and variants thereof, are produced by recombinant methods. Isolated DNA used in these methods is understood herein to mean chemically synthesized DNA, cDNA, chromosomal, or extrachromosomal DNA with or without the 3'- and/or 5'-flanking regions. Preferably, the VEGF and variants thereof herein are made by synthesis in recombinant cell culture.

For such synthesis, it is first necessary to secure nucleic acid that encodes a VEGF or VEGF variant. DNA encoding a VEGF molecule may be obtained from bovine pituitary follicular cells by (a) preparing a cDNA library from these cells, (b) conducting hybridization analysis with labeled DNA encoding the VEGF or fragments thereof (up to or more than 100 base pairs in length) to detect clones in the library containing homologous sequences, and (c) analyzing the clones by restriction enzyme analysis and nucleic acid sequencing to identify full-length clones. If full-length clones are not present in a cDNA library, then appropriate fragments may be recovered from the various clones using the nucleic acid sequence information disclosed herein for the first time and ligated at restriction sites common to the clones to assemble a full-length clone encoding the VEGF. Alternatively, genomic libraries will provide the desired DNA.

Once this DNA has been identified and isolated from the library, it is ligated into a replicable vector for further cloning or for expression.

In one example of a recombinant expression system, a VEGF-encoding gene is expressed in a cell system by transformation with an expression vector comprising DNA encoding the VEGF. It is preferable to transform host cells capable of accomplishing such processing so as to obtain the VEGF in the culture medium or periplasm of the host cell, i.e., obtain a secreted molecule.

"Transfection" refers to the taking up of an expression vector by a host cell whether or not any coding sequences are in fact expressed. Numerous methods of transfection are known to the ordinarily skilled artisan, for example, CaPO$_4$ and electroporation. Successful transfection is generally recognized when any indication of the operation of this vector occurs within the host cell.

"Transformation" refers to introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described by Cohen, *Proc. Natl. Acad. Sci. (USA),* 69: 2110 (1972) and Mandel et al. *J. Mol. Biol.,* 53: 154 (1970), is generally used for prokaryotes or other cells that contain substantial cell-wall barriers. For mammalian cells without such cell walls, the calcium phosphate precipitation method of Graham and van der Eb, *Virology,* 52: 456-457 (1978), is preferred. General aspects of mammalian cell host system transformations have been described by Axel in U.S. Pat. No. 4,399,216 issued Aug. 16, 1983. Transformations into yeast are typically carried out according to the method of Van Solingen et al. *J. Bact.,* 130: 946 (1977) and Hsiao et al. *Proc. Natl. Acad. Sci. (USA),* 76: 3829 (1979). However, other methods for introducing DNA into cells such as by nuclear injection or by protoplast fusion may also be used.

The vectors and methods disclosed herein are suitable for use in host cells over a wide range of prokaryotic and eukaryotic organisms.

In general, of course, prokaryotes are preferred for the initial cloning of DNA sequences and construction of the vectors useful in the invention. For example, *E. coli* K12 strain MM 294 (ATCC No. 31,446) is particularly useful. Other microbial strains that may be used include *E. coli* strains such as *E. coli* B and *E. coli* X1776 (ATCC No. 31,537). These examples are, of course, intended to be illustrative rather than limiting.

Prokaryotes may also be used for expression. The aforementioned strains, as well as *E. coli* strains W3110 (F—, lambda-, prototrophic, ATCC No. 27,325), K5772 (ATCC No. 53,635), and SR101, bacilli such as *Bacillus subtilis*, and other enterobacteriaceae such as *Salmonella typhimurium* or *Serratia marcesans*, and various pseudomonas species, may be used.

In general, plasmid vectors containing replicon and control sequences that are derived from species compatible with the host cell are used in connection with these hosts. The vector ordinarily carries a replication site as well as marking sequences that are capable of providing phenotypic selection in transformed cells. For example, *E. coli* is typically transformed using pBR322, a plasmid derived from an *E. coli* species (see, e.g., Bolivar et al. *Gene,* 2:95 (1977). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the β-lactamase (penicillinase) and lactose promoter systems Chang et al. *Nature,* 375:615 (1978); Itakura et al. *Science,* 198:1056 (1977); Goeddel et al. *Nature,* 281:544 (1979)) and a tryptophan (trp) promoter system (Goeddel et al. *Nucleic Acids Res.,* 8:4057 (1980); EPO Appl. Publ. No. 0036,776). While these are the most commonly used, other microbial promoters have been discovered and utilized, and details concerning their nucleotide sequences have been published, enabling a skilled worker to ligate them functionally with plasmid vectors (see, e.g., Siebenlist et al. *Cell,* 20:269 (1980)).

In addition to prokaryotes, eukaryotic microbes, such as yeast cultures, may also be used. *Saccharomyces cerevisiae*, or common baker's yeast, is the most commonly used among eukaryotic microorganisms, although a number of other strains are commonly available. For expression in *Saccharomyces*, the plasmid YRp7, for example (Stinchcomb et al. *Nature,* 282:39 (1979); Kingsman et al. *Gene,* 7:141 (1979); Tschemper et al. *Gene,* 10:157 (1980)), is commonly used. This plasmid already contains the trp1 gene that provides a selection marker for a mutant strain of yeast lacking the ability to grow in tryptophan, for example, ATCC No. 44,076 or PEP4-1 (Jones, *Genetics,* 85:12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al. *J. Biol. Chem.,* 255:2073 (1980)) or other glycolytic enzymes (Hess et al. *J. Adv. Enzyme Reg.,* 7:149 (1968); Holland et al. *Biochemistry,* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (Tissue Culture, Academic Press, Kruse and Patterson, editors (1973)). Examples of such useful host cell lines are VERO and HeLa cells, Chinese hamster ovary (CHO) cell lines, and W138, BHK, COS-7, 293, and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication (Fiers et al. *Nature,* 273:113 (1978)). Smaller or larger SV40 fragments may also be used, provided there is included the approximately 250-bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Satisfactory amounts of protein are produced by cell cultures; however, refinements, using a secondary coding sequence, serve to enhance production levels even further. One secondary coding sequence comprises dihydrofolate reductase (DHFR) that is affected by an externally controlled parameter, such as methotrexate (MTX), thus permitting control of expression by control of the methotrexate concentration.

In selecting a preferred host cell for transfection by the vectors of the invention that comprise DNA sequences encoding both VEGF and DHFR protein, it is appropriate to select the host according to the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Natl. Acad. Sci.* (*USA*), 77:4216 (1980).

On the other hand, if DHFR protein with low binding affinity for MTX is used as the controlling sequence, it is not necessary to use DHFR-deficient cells. Because the mutant DHFR is resistant to methotrexate, MTX-containing media can be used as a means of selection provided that the host cells are themselves methotrexate sensitive. Most eukaryotic cells that are capable of absorbing MTX appear to be methotrexate sensitive. One such useful cell line is a CHO line, CHO-K1 (ATCC No. CCL 61).

Construction of suitable vectors containing the desired coding and control sequences employs standard ligation techniques. Isolated plasmids or DNA fragments are cleaved, tailored, and religated in the form desired to prepare the plasmids required.

If blunt ends are required, the preparation may be treated for 15 minutes at 15° C. with 10 units of Polymerase I (Klenow), phenol-chloroform extracted, and ethanol precipitated.

Size separation of the cleaved fragments may be performed using, by way of example, 6 percent polyacrylamide gel described by Goeddel et al. *Nucleic Acids Res.*, 8:4057 (1980).

To confirm correct sequences were constructed in plasmids, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al. *Nucleic Acids Res.*, 9:309 (1981) or by the method of Maxam et al. *Methods of Enzymology*, 65:499 (1980).

After introduction of the DNA into the mammalian cell host and selection in medium for stable transfectants, amplification of DHFR-protein-coding sequences is effected by growing host cell cultures in the presence of approximately 20,000-500,000 nM concentrations of methotrexate (MTX), a competitive inhibitor of DHFR activity. The effective range of concentration is highly dependent, of course, upon the nature of the DHFR gene and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

In some aspects of the invention, the Flt-1 agonist comprises a growth factor that selectively binds to and activates Flt-1. Several naturally occurring VEGF homologues that specifically bind to Flt-1 but not KDR have been identified, including without limiting to, placental growth factor (PIGF) and VEGF-B. PIGF has an amino acid sequence that shares 53% identity with the platelet-derived growth factor-like domain of VEGF. Park et al. (1994) *J. Biol. Chem.* 269: 25646-54; Maglione et al. (1993) *Oncogene* 8:925-31. As with VEGF, different species of PIGF arise from alternative splicing of mRNA, and the protein exists in dimeric form. Park et al., supra. Both PIGF-1 and PIGF-2 bind to Flt-1 with high affinity, but neither is able to interact with KDR. Park et al., supra.

VEGF-B is produced as two isoforms (167 and 185 residues) that also appear to specifically bind Flt-1. Pepper et al. (1998) *Proc. Natl. Acad. Sci. USA* 95:11709-11714. Similar to the long forms of VEGF, VEGF-B is expressed as a membrane-bound protein that can be released in a soluble form after addition of heparin. VEGF-B and VEGF are also able to form heterodimers, when coexpressed. Olofsson et al. (1996) *Proc. Natl. Acad. Sci. USA* 93:2576-2581.

Compounds useful in the invention include small oraganic molecules that exert their modulating functions at the intracellular tyrosine kinase domain of the RTKs. In certain preferred embodiments, small molecule agonists are employed to stimulate tyrosine phosphorylation, thereby activating the corresponding signaling pathway. In other embodiments, small molecule inhibitors or antagonists are used to block and/or deactivate the RTK activities. Many small molecule compounds can be used for the purpose of this invention. These include, but not limited to, bis monocyclic, bicyclic or heterocyclic aryl compounds, vinylene-azaindole derivatives (PCT WO 94/14808) and 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (EP Application No. 0 566 266 A1), selenoindoles and selenides (PCT WO 94/03427), tricyclic polyhydroxylic compounds (PCT WO 92/21660) and benzylphosphonic acid compounds (PCT WO 91/15495).

Compounds useful in the present invention include agonist or antagonist antibodies. Antibodies of the present invention can be either specific against a receptor (such as Flt-1), or specific against a ligand of the receptor, so long as they exert the necessary agonistic or antagonistic activity. Preferred antibodies of the invention include anti-Flt-1 antibodies. More preferably, the anti-Flt-1 antibody selectively binds to and modulate Flt-1, without affecting the KDR function.

The term "antibody" is used in the broadest sense and includes monoclonal antibodies (including full length or intact monoclonal antibodies), polyclonal antibodies, multivalent antibodies, multispecific antibodies (e.g., bispecific antibodies), and antibody fragments so long as they exhibit the desired biological activity. It is also contemplated that non-human antibodies, chimeric antibodies, humanized antibodies or human antibodies can be used for the purpose of the invention. Methods of preparing various antibodies suitable for the invention are known to the skilled artisan.

A naturally occurring antibody comprises four polypeptide chains, two identical heavy (H) chains and two identical light (L) chains inter-connected by disulfide bonds. Each heavy chain is comprised of a heavy chain variable region ($V_H$) and a heavy chain constant region, which in its native form is comprised of three domains, CH1, CH2 and CH3. Each light chain is comprised of a light chain variable region ($V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The light chains of antibodies from any vertebrate species can be assigned to one of two clearly distinct types, called kappa (κ) and lambda (λ), based on the amino acid sequences of their constant domains. Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG-1, IgG-2, IgA-1, IgA-2, and etc. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or noncovalent association of the antibody or antibody portion with one or more other proteins or peptides. Examples of such fusion proteins include use of the streptavidin core region to make a tetrameric scFv molecule (Kipriyanov et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058).

Other agents capable of modulating Flt-1 or KDR activities include, for example but not limited to, soluble extracellular domain peptides of Flt-1 or KDR, Flt-1 or KDR binding peptides, Flt-1 or KDR specific ribozymes, antisense polynucleotides and RNA ligands. For example, soluble Flt-1 extracellular fragments as antagonists are described in U.S. Pat. No. 6,100,071.

Assay Methods of the Invention

In one aspect, the invention provides methods of using VEGFR agonists to upregulate gene expressions of factors that are important in regulating liver activities. In a preferred embodiment, the expression of HGF in nonparenchymal cells is upregulated. Methods and techniques for detecting levels of mRNA expression or protein expression in target cells/tissues are known to those skill in the art. For example, the HGF gene expression level can be detected by known nucleic acid hybridization assays, using probes capable of hybridizing to HGF polynucleotides, under conditions suitable for the hybridization and subsequent detection and measurement. Methods useful for detecting HGF gene expression include but not limited to southern hybridization (Southern (1975) *J. Mol. Biol.* 98:503-517), northern hybridization (see, e.g., Freeman et al. (1983) *Proc. Natl. Acad. Sci. USA* 80:4094-4098), restriction endonuclease mapping (Sambrook et al. (1989) Molecular Cloning, A Laboratory Manual, 2nd Ed. Cold Spring Harbor Laboratory Press, New York), RNase protection assays (Current Protocols in Molecular Biology, John Wiley and Sons, New York, 1997), DNA sequence analysis, and polymerase chain reaction amplification (PCR; U.S. Pat. Nos. 4,683,202, 4,683,195, and 4,889,818; Gyllenstein et al. 1988, *Proc Natl. Acad. Sci. USA* 85:7652-7657; Ochman et al. 1988, *Genetics* 120:621-623; Loh et al. 1989, *Science* 243:217-220) followed by Southern hybridization with probes specific for the HGF gene, in various cell types. Other methods of amplification commonly known in the art can be employed. The stringency of the hybridization conditions for northern or Southern blot analysis can be manipulated to ensure detection of nucleic acids with the desired degree of relatedness to the specific probes used. The expression of HGF in a cell or tissue sample can also be detected and quantified using in situ hybridization techniques according to, for example, Current Protocols in Molecular Biology, John Wiley and Sons, New York, 1997.

The HGF protein levels can be detected by immunoassays using antibodies specific to HGF. Various immunoassays known in the art can be used, including but not limited to competitive and non-competitive assay systems using techniques such as radioimmunoassay, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels), western blot analysis, precipitation reactions, agglutination assays (e.g., gel agglutination assays, hemagglutination assays), complement fixation assays, immunofluorescence assays, protein A assays, immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

The invention provides methods for promoting liver growth and hepatocyte cell proliferation by administering an effective amount of VEGFR agonists. The promoting effects of the present invention can be assessed either in vitro or in vivo, using methods known in the art. Drakes et al. (1997) *J. Immunol.* 159:4268; Omori et al. (1997) *Hepatology* 26:720; U.S. Pat. No. 5,227,158.

In one embodiment of the invention, hepatocytes and other nonparenchymal liver cells are isolated from the target livers and resuspended in appropriate tissue culture medium to induce cell adherence. If necessary, different cell fractions can be further separated (e.g., parenchymal cells from nonparenchymal cells) by centrifugation at different speeds for different length of time. Cell proliferation is assessed during culture using methods known in the art, including but not limited to, measuring the rate of DNA synthesis (see, e.g., Nakamura et al. (1984) supra), trypan blue dye exclusion/ hemacytometer counting (see, e.g., Omiri et al. (1997) supra), or flow cytometry (see, e.g., Drakes (1997) supra).

In another embodiment, the proliferative effect of a VEGFR agonist on hepatic cells and liver organ as a whole is measured in vivo using, for example, histochemistry assays of the liver tissue samples. In a preferred aspect, in vivo proliferation of hepatic cells is assessed by reactivity to an antibody directed against a protein known to be present in higher concentrations in proliferating cells than in non-proliferating cells, such as proliferating cell nuclear antigen (PCNA or cyclin). Rodgers et al. (1997) *J. Burn Care Rehabil.* 18:381-388. A more preferred method is the BrdU immunohistochemistry assay as previously described by Gerber et al. (1999) *Development* 126:1149-1159.

Treatment of Pathological Liver Conditions

According to one embodiment, the invention provides methods for treating a pathological liver condition in a subject. As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

An "effective amount" refers to an amount effective, at dosages and for periods of time necessary, to achieve the desired therapeutic or prophylactic result. A "therapeutically effective amount" of the antibody may vary according to factors such as the disease state, age, sex, and weight of the individual, and the ability of the antibody to elicit a desired response in the individual. A therapeutically effective amount is also one in which any toxic or detrimental effects of the antibody are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The phrase "pathological liver condition" is used interchangeably with "liver disorder" or "liver disease" to indicate any structural and/or functional liver abnormalities. Non-limiting examples of pathological liver condition include those conditions associated with liver failure, hepatitis (acute, chronic or alcohol), liver cirrhosis, toxic liver damage, medicamentary liver damage, hepatic encephalopathy, hepatic coma or hepatic necrosis.

Protection Against Liver Damage

In one aspect, the invention provides methods for protecting liver from damage in a subject susceptible to conditions or factors causative of liver damage. The phrase "liver damage" is used herein in the broadest sense, and indicates any structural or functional liver injury resulting, directly or indirectly, from internal or external factors or their combinations. Liver damage can be induced by a number of factors including, but not limited to, exposure to hepatotoxic compounds, radiation exposure, mechanical liver injuries, genetic predisposition, viral infections, autoimmune disease, such as, autoimmune chronic hepatitis and as a result of elevated in vivo levels of proteins, such as activin and TGF-.beta.

Liver damage induced by hepatotoxic compounds includes direct cytotoxicity including drug hypersensitivity reactions, cholestasis, and injury to the vascular endothelium.

A number of hepatotoxic compounds, including certain therapeutics, induce cytotoxicity. Hepatotoxic compounds can produce liver cytotoxicity by direct chemical attack or by the production of a toxic metabolite. Although the exact mechanism of hepatotoxicity is uncertain, the products of reductive metabolism are highly reactive species that bind to cellular macromolecules and cause lipid peroxidation and inactivation of drug metabolizing and other enzymes. The membrane injury provokes release of calcium from mitochondria and smooth endoplasmic reticulum and appears to interfere with the calcium ion pump, which normally prevents cytosolic accumulation of calcium. The deleterious effect on cell metabolism with resultant calcium accumulation, the loss of potassium and enzymes from the cytoplasm, and the loss of essential energy that results from mitochondrial injury all contribute to the necrosis of hepatic tissue.

Many hepatotoxic compounds unpredictably produce liver damage in a small proportion of recipients. In some patients, the liver damage is referred to as a hypersensitivity reaction and is like that of a drug reaction, where the patient presents with fever, rash and eosinophilia and has a recurrence of symptoms upon rechallenge of the drug. In other situations, the mechanism for injury is unknown and may represent aberrant metabolism in susceptible patients that permits the production or accumulation of hepatotoxic metabolites.

Those drugs inducing cytotoxicity by direct chemical attack include the following: Anesthetics, such as Enflurane, Fluroxene, Halothane, and Methoxyflurane; Neuropsychotropics, such as, Cocaine, Hydrazides, Methylphenidate, and Tricyclics; Anticonvulsants, such as, Phenytoin and Valproic acid; Analgesics, such as, Acetaminophen, Chlorzoxazone, Dantrolene, Diclofenac, Ibuprofen, Indomethacin, Salicylates, Tolmetin, and Zoxazolamine; Hormones, such as, Acetohexamide, Carbutamide, Glipizide, Metahexamide, Propylthiouracil, Tamoxifen, Diethylstilbestrol; Antimicrobials, such as, Amphotericin B, Clindamycin, Ketoconazole, Mebendazole, Metronidazole, Oxacillin, Paraminosalicylic acid, Penicillin, Rifampicin, Sulfonamides, Tetracycline, and Zidovudine; Cardiovascular drugs, such as, Amiodarone, Dilitiazem, a-Methyldopa, Mexiletine, Hydrazaline, Nicotinic acid, Papaverine, Perhexiline, Procainamide, Quinidine, and Tocainamide; and Immunosuppressives and Antineoplastics, such as, Asparaginase, Cisplatin, Cyclophosphamide, Dacarbazine, Doxorubicin, Fluorouracil, Methotrexate, Mithramycin, 6-MP, Nitrosoureas, Tamoxifen, Thioguanine, and Vincristine; and Miscellaneous drugs, such as, Disulfiram, Iodide ion, Oxyphenisatin, Vitamin A and Paraminobenzoic acid.

Those hepatotoxic compounds producing hypersensitivity reaction in the liver include the following: Phenyloin, Paramino salicylic acid, Chlorpromazine, Sulfonamides, Erythromycin estolate, Isoniazid, Halothane, Methyldopa, and Valproic acid.

Hepatotoxic compounds including cholestasis, an arrest in the flow of bile, may take several forms. Centribular cholestasis is accompanied by portal inflammatory changes. Bile duct changes have been reported with some drugs such as erythromycin, while pure canalicular cholestasis is characteristic of other drugs such as the anabolic steroids. Chronic cholestasis has been linked to such drugs as methyltestosterone and estradiol.

Those hepatotoxic compounds inducing cholestatic disease include the following: Contraceptive steroids, androgenic steroids, anabolic steroids, Acetylsalicylic acid, Azathioprine, Benzodiazepine, Chenodeoxycholic acid, Chlordiazepoxide, Erythromycin estolate, Fluphenazine, Furosemide, Griseofulvin, Haloperidol, Imipramine, 6-Mercaptopurine, Methimazole, Methotrexate, Methyldopa, Methylenediamine, Methyltestosterone, Naproxen, Nitrofurantoin, Penicillamine, Perphenazine, Prochlorperazine, Promazine, Thiobendazole, Thioridazine, Tolbutamide, Trimethoprimsulfamethoxazole, Arsenic, Copper, and Paraquat.

Some drugs, although primarily cholestatic, can also produce hepatoxicity, and therefore the liver injury they cause is mixed. The drugs causing mixed liver injury include, for example, the following: Chlorpromazine, Phenylbutazone, Halothane, Chlordiazepoxide, Diazepam, Allopurinol, Phenobarbital, Naproxen, Propylthiouracil, Chloramphenicol, Trimethoprimsulfamethoxazxole, Amrinone, Disopyramide, Azathioprine, Cimetidine, and Ranitidine.

Vascular lesions of the liver, including thrombosis of the hepatic veins, occlusion of the hepatic venules or veno occlusive disease (VOD), and peliosis hepatitis, can be produced by drugs. In addition, lesions including sinusoidal dilation, perisinusoidal fibrosis, and hepatoportal selerosis can occur. Midzonal and pericentral sinusoidal dilatation was first reported as a complication of oral contraceptive therapy.

Peliosis hepatitis is a condition consisting of large blood-filled cavities that results from leakage of red blood cells through the endothelial barrier, followed by perisinusoidal fibrosis. It has been described in patients taking oral contraceptives, anabolic steroids, azathioprine and danazol. Injury and occlusion of the central hepatic venules is also known to be related to the ingestion of pyrrolizidine alkaloids, such as bush teas. The initial lesion is central necrosis accompanied by a progressive decrease in venule caliber. All of these lesions may be only partially reversible when the drug is stopped and cirrhosis can develop.

Several types of benign and malignant hepatic neoplasm can result from the administration of hepatotoxic compounds. Adenomas, a lesion restricted to women in the childbearing years, is related to the use of contraceptive steroids and the risk increases with duration of use. Hepatocellular carcinoma may also be seen in patients taking androgenic hormones for aplastic anemia or hypopituitarism.

Hepatotoxic compounds known to cause hepatic liesons include the following: Contraceptive steroids, Pyrriolizidine alkaloids, Urethane, Azathioprine, 6-Mercaptopurine, 6-Thioguanine, Mitomycin, BCNU, Vincristine, Adriamycin, Intravenous Vitamin E, Anabolic-androgenic steroids, Azathioprine, Medroxyprogesterone acetate, Estrone sulfate, Tamoxifen, inorganic arsenicals, Thorium dioxide, Vitamin A, methotrexate, Methylamphetamine hydrochloride, Vitamin A, Corticosteroids, Thorium dioxide, and Radium therapy.

Liver damage caused by other factors usually takes similar forms. Liver damage, whether caused by the hepatotoxicity of a compound, radiation therapy, genetic predisposition, mechanical injury or any combination of such and other factors, can be detected by several means. Biochemical tests have been used clinically for many years as the standard measure of hepatotoxicity. Most biochemical tests generally fall into two categories: tests which measure specific liver markers, for example, prothrombin clotting time, and/or hepatic blood flow, or tests which analyze serum markers, for detection of necrosis, cholestasis, progressive fibrogenesis, or hepatoma (Cornelius, C. in Hepatotoxicology, Meeks et al. eds., pgs. 181-185 (1991)). The importance of such tests lies in their simplicity and the fact that they are non-invasive. The rationale for the use of serum enzymes in assessing liver damage is that these enzymes, normally contained in the liver cells, gain entry into the general circulation when liver cells are injured.

Elevated serum enzyme activity suggests nercrosis and/or cholestasis. Elevated levels of serum bilirubin conjugates suggest intra or extra hepatic cholestasis. However, there are certain limitations for the use of serum enzyme levels as single means of diagnosing liver injury. Serum enzyme levels may increase as a result of leakage from cells with altered permeability due to systemic effects of an agent rather than specific liver injury caused by a chemical. Histopathological examination of the liver is the next logical step in identifying and quantifying the nature and extent of liver injury.

The serum enzymes as markers of liver injury can be divided into four groups based on specificity and sensitivity to liver damage (Kodavanti et al., Supra).

Group I: these enzymes indicate more selectively hepatic cholestasis when elevated, e.g. alkaline phosphatase (AP), 5'-nucleotidase (5'-ND), and a-glutamyl transpeptidase (G-GT) and leucine aminopeptidase (LAP).

Group II: These enzymes indicate parenchymal injury when elevated, e.g., aspartate transaminase (AST), alanine transaminase (ALT), fructose-1,6-diphosphate aldolase (ALD), lactate dehydrogenase (LDH), isocitrate dehydrogenase (ICDH), ornithine-carbamoyl-transferase (OCT), and sorbitol dehydrogenase (SDH) arginase and guanase.

Group III: These enzymes represent injury of other tissue when elevated e.g., creatine phosphokinase (CPK).

Group IV: These enzymes are depressed in hepatic injury, e.g., cholinesterase (ChE).

Other serum markers include, procollagen type III peptide levels (PIIIP) to assess if hepatic fibrogenesis is active; ammonia blood levels in hepatoencephalopathies; ligand in levels in necrosis and hepatoma; hyaluronate levels due to hepatic endothelial cell damage; a-1-fetoprotein (AFP) levels to detect hepatoma; carcinoembryonic antigen (CEA) levels to detect cancer metastasis to the liver; elevations of antibodies against a variety of cellular components, such as, mitochondrial, and nuclear and specific liver membrane protein; and detection of proteins, such as, albumin, globin, amino acids, cholesterol, and other lipids. Also, biochemical analysis of a variety of minerals, metabolites, and enzymes obtained from liver biopsies can be useful in studying specific biochemical defects in inherited, acquired, and experimentally induced liver disorders.

Liver function tests can be performed to assess liver injury. Liver function tests include the following:

Group I assessment of hepatic clearance of organic anions, such as, bilirubin, indocyanine green (ICG), sulfobromophthalein (BSP) and bile acids;

Group II assessment of hepatic blood flow by measurements of galactose and ICG clearance;

and Group III assessment of hepatic microsomal function, through the use of the aminopyrine breath test and caffeine clearance test. For example, serum bilirubin can be measured to confirm the presence and severity of jaundice and to determine the extent of hyperbilirubinemia, as seen in parenchymal liver disease. Aminotransferase (transaminase) elevations reflect the severity of active hepatocellular damage, while alkaline phosphatase elevations are found with cholestasis and hepatic infiltrates (Isselbacher, K. and Podolsky, D. in Hartison's Principles of Internal Medicine, 12th edition, Wilson et al. eds., 2:1301-1308 (1991)). Methods for performing serum enzyme analysis are known in the art and are, for example, described in Kodavanti et al. Supra.

Because extensive liver injury may lead to decreased blood levels of albumin, prothrombin, fibrinogen, and other proteins synthesized exclusively by hepatocytes, these protein levels may be measured as indicators of liver injury. In contrast to measurements of serum enzymes, serum protein levels reflect liver synthetic function rather than just cell injury (Podolsky, D. Principles of Internal Medicine, 12th edition, Wilson et al. eds., 2: 1308-1311 (1991)).

In many patients, computed tomography (CT), ultrasound, scintiscans, or liver biopsy may be needed to determine the nature of the liver disease (Isselbacher, K, Supra and Friedman, L. and Needleman, L. in Harrison's Principles of Internal Medicine, 12th edition, Wilson et al. eds., 2: 1303-1307 (1991)).

The present invention provides methods for enhancing the effect of chemotherapy of cancer in a subject, said methods comprising administering to the subject a VEGFR modulating agent in a manner effective to protect the liver of the subject from damage caused by a hepatoxic compound prior to, or simultaneous with, the chemotherapy, thereby increasing the subject's tolerance to the chemotherapy. The chemotherapeutic agents used during the course of chemotherapy can have cytotoxic effects upon hepatic cells, therefore limiting the dosage and/or duration of the chemotherapeutic agent being administered to the patient. By exposing the liver to a composition comprising a VEGFR agonist such as VEGF, Flt-sel or KDR-sel, such toxic effects can be prevented or reduced. As such, the dosage of the chemotherapeutic agents can be increased, thereby enhancing the efficacy of the cancer therapy.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin $\gamma_1^I$ and calicheamicin $\theta_1^I$, see, e.g., Agnew $Chem\ Intl.\ Ed.\ Engl.$ 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Pharmaceutical Compositions and Therapeutic/prophylactic Administration

For in vivo uses according to the methods of the invention, a therapeutic compound of the invention is administered to a subject using methods and techniques known in the art and suitable for the particular use. In a preferred embodiment, the compound is administered in the form of pharmaceutical compositions at a pharmaceutically acceptable dosage.

In one aspect, the invention contemplates the use of mammalian cell preparations for the administration of a therapeutic protein agent (such as VEGF, Flt-sel or KDR-sel). The mammalian cells used herein have been transfected with the heterologous gene encoding the protein, as described in detail above. In a preferred embodiment, the host cells used for the administration are CHO cells.

In another aspect of the invention, the therapeutic agent can be entrapped in microcapsules prepared, for example, by coacervation techniques or by interfacial polymerization, in colloidal drug delivery systems (e.g., liposomes, microspheres, microemulsions, nanoparticles and nanocapsules), or in macroemulsions. Such techniques are known in the art and disclosed in Remington, the Science and Practice of Pharmacy, 20th Edition, Remington, J., ed. (2000).

In one aspect of the invention, the therapeutic agent can be administered in vivo in slow-release preparations. Suitable examples of slow-release preparations include semipermeable matrices of solid hydrophobic polymers containing the multivalent antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The therapeutic composition of the invention can be administered by any suitable means, including but not limited to, parenteral, subcutaneous, intraperitoneal, intrapulmonary, and intranasal administration. Parenteral infusions include intramuscular, intravenous, intraarterial, intraperitoneal, or subcutaneous administration. In addition, the therapeutic composition is suitably administered by pulse infusion, particularly with declining doses of the antibody. Preferably the therapeutic composition is given by injections, most preferably intravenous or subcutaneous injections, depending in part on whether the administration is brief or chronic.

It is further contemplated that a therapeutic protein agent of the invention (such as VEGF, Flt-sel or KDR-sel) can be introduced to a subject by gene therapy. Gene therapy refers to therapy performed by the administration of a nucleic acid to a subject. For general reviews of the methods of gene therapy, see, for example, Goldspiel et al. (1993) Clinical Pharmacy 12:488-505; Wu and Wu (1991) Biotherapy 3:87-95; Tolstoshev (1993) Ann. Rev. Pharmacol. Toxicol. 32:573-596; Mulligan (1993) Science 260:926-932; Morgan and Anderson (1993) Ann. Rev. Biochem. 62:191-217; and May (1993) TIBTECH 11: 155-215. Methods commonly known in the art of recombinant DNA technology which can be used are described in Ausubel et al. eds. (1993) Current Protocols in Molecular Biology, John Wiley & Sons, NY; and Kriegler (1990) Gene Transfer and Expression, A Laboratory Manual, Stockton Press, NY.

There are two major approaches to getting the nucleic acid (optionally contained in a vector) into the subject's cells; in vivo and ex vivo. For in vivo delivery the nucleic acid is injected directly into the subject, usually at the site where the protein is required. For ex vivo treatment, the subject's cells are removed, the nucleic acid is introduced into these isolated cells and the modified cells are administered to the subject either directly or, for example, encapsulated within porous membranes which are implanted into the subject (see, e.g. U.S. Pat. Nos. 4,892,538 and 5,283,187). There are a variety of techniques available for introducing nucleic acids into viable cells. The techniques vary depending upon whether the nucleic acid is transferred into cultured cells ex vivo, or in vivo in the cells of the intended host. Techniques suitable for the transfer of nucleic acid into mammalian cells ex vivo include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, lentivirus, retrovirus, or adeno-associated virus) and lipid-based systems (useful lipids for lipid-mediated transfer of the gene are DOTMA, DOPE and DC-Chol, for example). Examples of using viral vectors in gene therapy can be found in Clowes et al. (1994) J. Clin. Invest. 93:644-651; Kiem et al. (1994) Blood 83:1467-1473; Salmons and Gunzberg (1993) Human Gene Therapy 4:129-141; Grossman and Wilson (1993) Curr. Opin. in Genetics and Devel. 3:110-114; Bout et al. (1994) Human Gene Therapy 5:3-10; Rosenfeld et al. (1991) Science 252:431-434; Rosenfeld et al. (1992) Cell 68:143-155; Mastrangeli et al. (1993) J. Clin. Invest. 91:225-234; and Walsh et al. (1993) Proc. Soc. Exp. Biol. Med. 204:289-300.

In some situations it is desirable to provide the nucleic acid source with an agent that targets the target cells, such as an antibody specific for a cell surface membrane protein on the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al. *J. Biol. Chem.* 262:4429-4432 (1987); and Wagner et al. *Proc. Natl. Acad. Sci. USA* 87:3410-3414 (1990). For review of the known gene marking and gene therapy protocols see Anderson et al. Science 256:808-813 (1992).

The present invention also provides pharmaceutical compositions. Such compositions comprise a therapeutically effective amount of a VEGFR modulating agent, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated, in accordance with routine procedures, as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent.

Where the composition is to be administered by infusion, it can be dispensed with an infusion bottle containing sterile pharmaceutical grade water or saline. Where the composition is administered by injection, an ampoule of sterile water or saline for injection can be provided so that the ingredients may be mixed prior to administration.

The therapeutics of the invention can be formulated as neutral or salt forms. Pharmaceutically acceptable salts include those formed with free carboxyl groups such as those derived from hydrochloric, phosphoric, acetic, oxalic, tartaric acids, etc., those formed with free amine groups such as those derived from isopropylamine, triethylamine, 2-ethylamino ethanol, histidine, procaine, etc., and those derived from sodium, potassium, ammonium, calcium, and ferric hydroxides, etc. The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The following examples are intended merely to illustrate the practice of the present invention and are not provided by way of limitation. The disclosures of all patent and scientific literatures cited herein are expressly incorporated in their entirety by reference.

EXAMPLES

Example 1

VEGFR Selective Variants of VEGF

Generation and characterization of VEGF variants that selectively bind and activate a specific VEGF receptor (such as KDR or Flt-1) have been known in the art and described in, for example, Li et al. (2000) *J. Biol. Chem.* 275:29823; Gille et al. (2001) *J. Biol. Chem.* 276:3222-3230; PCT publications WO 00/63380 and 97/08313; and U.S. Pat. No. 6,057,428, the disclosure of which are expressly incorporated herein by reference.

Specifically, a VEGF variant with high selectivity for the Flt-1 receptor was generated by combining four mutations that greatly affected KDR but not Flt-1 binding. Mutation to alanine of Ile 43, Ile 46, Gln 79 or Ile 83 showed that the side chains of these residues are critical for tight binding to KDR but unimportant for Flt-1-binding. Li et al. (2000) supra. A Flt-sel variant was constructed with alanine substitutions at positions Ile 43, Ile 46, Gln 79 and Ile 83, using site directed mutagenesis methods described by Kunkel et al. (1991) *Methods Enzymol.* 204:125-139. This particular Flt-sel variant can also be represented by the identifier, I43A/I46A/Q79A/I183A. The corresponding codons for these four alanine substitutions at positions 43, 46, 79 and 83 are GCC/GCC/GCG/GCC, respectively.

Various assays were conducted to examine the properties and biological activities of the I43A/I46A/Q79A/I83A Flt-sel variant. Li et al. (2000) supra. For example, quantitative binding measurements were carried out using a soluble radio-immuno receptor-binding assay (RIA). In the assay, native VEGF(8-109) had affinities for KDR and Flt-1 of 0.5 nM and 0.4 nM, respectively. Flt-sel was found to have at least 470-fold reduced KDR-binding affinity in this assay. Somewhat surprisingly, since small reductions in Flt-1-binding had been observed from the individual point mutants in the ELISA, the Flt-sel variant's affinity for Flt-1 was essentially identical to that of the native protein.

Example 2

Promotion of Liver Growth

Methods and Materials

The full-length cDNA encoding for human $VEGF_{165}$ (Leung et al. (1989) *Science* 246:1306-9) was inserted into the dicistronic dihydrofolate reductase (DHFR) intron expression vector SV.DI (Lucas et al. (1996) *Nucleic Acids Res.* 24:1774-9), resulting in the construct SV.DI.$VEGF_{165}$.H8. A control construct, SV.DI.HAg.H8, was similarly constructed using cDNA encoding for Hakata antigen (HAg) as insert. HAg is a serum glycoprotein which has been recently shown to be an autoantigen in systemic lupus erythematosus patients. Sugimoto et al. (1998) *J. Biol. Chem.* 273:20721-7. This protein has structural homology to the angiopoietin family, although it does not interact with the Tie-2 receptor.

Using either construct described above, a dicistronic mRNA was transcribed under the control of the SV40 early gene promoter and encoded both the DHFR gene and the inserted gene of interest, which were thereby expressed in a fixed equimolar ratio. Both open reading frames were also fused with a DNA sequence encoding for a short carboxyl terminal peptide tag consisting of 8 histidine residues allowing easy detection and purification. The linearized expression plasmids, SV.DI.$VEGF_{165}$.H8, and SV.DI.HAg.H8 as well as an empty vector, SV.DI.H8, were electroporated into $DHFR^-$ CHO cells. Prior to transfection, these cells were grown in growth medium consisting of F12/DMEM-based medium containing high concentrations of amino acids and insulin supplemented with 10% FBS, L-glutamine (2 mM.), glycine (10 μg/ml), hypoxanthine (15 μg/ml), and thymidine (5 μg/ml)(GHT). Pools of stably transfected $DHFR^+$ CHO cells were derived and maintained by selection in GHT-free rich medium (Lucas et al. (1996) *Nucleic Acids Res.* 24:1774-9). Expression of the $VEGF_{165}$ protein by $VEGF_{165}$ transfected CHO cells (CHO-$VEGF_{165}$) was confirmed by immunoblotting and ELISA. A band of ~23 kDa, which corresponds to the expected molecular weight of the $VEGF_{165}$ monomer, was immunoprecipitated from conditioned culture media of CHO-$VEGF_{165}$ cells. Such band was not present in culture supernatants of CHO-DHFR control cells.

For generation of CHO-HGF cells, the full length cDNA encoding for HGF was inserted into the pRK5 expression vector and transfected into CHO cells, as described previously (Zioncheck et al. (1995) *J. Biol. Chem.* 270:16871-8). HGF is a key mitogen for hepatocytes and has sequence similarity to plasminogen. Nakamura et al. (1987) *FEBS Lett.* 224:311-6. HGF is secreted as a single-chain 82-84 kDa promitogen which is endoproteolytically processed into the bioactive HGF heterodimer, consisting of a 69 kDa α-chain and a 32 kDa β-chain. Nakamura et al. (1987) *FEBS Lett* 224:311-6. A band consistent in molecular weight with the 69 kDa HGF α-chain was detected in conditioned culture media of CHO-HGF cells but not in CHO-DHFR controls. Using the control construct SV.DI.HAg.H8, another stably transfected CHO cell pool was also generated, which secretes high amounts of HAg. Under reducing conditions, the HAg monomer was detected in CHO-HAg conditioned culture media as a band of 32 kDa.

VEGF-PLGA microspheres were used as a slow release formulation of VEGF. VEGF-PLGA microspheres were generated by encapsulating $VEGF_{165}$ protein into poly(lactic-co-glycolic acid) biodegradable polymer (provided by J. Cleland and A. Daugherty, Genentech). About 10% of the total VEGF protein contained in the microspheres was released into the circulation.

Juvenile (3-4 week old) or adult athymic beige nude xid mice (Hsd:NIHS-bg-nu-xid, Harlan Sprague Dawley (Indianapolis, Ind.)) were anesthetized by isofluorane inhalation. Each group consisted of five animals. Suspensions of stably transfected or control CHO cells in complete culture medium were intramuscularly injected into both legs of the animal. A total volume of 100 µl cell suspensions containing about $3 \times 10^6$ cells was injected into 3 different sites of the anterior femoral muscles of each leg. On day 14 after injection, the mice were sacrificed, and serum samples were isolated and further analyzed.

VEGF-PLGA treated animals received a total of 3 intramuscular injections of 100 µl of PLGA-VEGF microspheres per leg at days 1, 7, and 10. The dose of released VEGF per injection was about 4.5 mg/kg. The VEGF-PLGA injected animals were sacrificed on day 15. One hour before sacrifice, all animals were intraperitoneally injected with 100 mg/kg bromodeoxyuridine (BrdU) (Sigma, St. Louis, Mo.). Livers, kidneys, heart, legs, and brains were removed and weighed. The collected tissues were immersed in formalin for histological evaluation.

For proliferation studies, animals were injected with BrdU (100 mg/kg) 1 hour prior to killing. Tissues were fixed in 10% neutral buffered formalin for 12 to 16 hours prior to paraffin embedding. BrdU immunohistochemoistry was performed as previously described. Gerber et al., (1999). A monoclonal rat anti-mouse antibody for F4/80 (Serotec, Raleigh, N.C.) was used at 10 µg/ml (1:1000 dilution) on 5 µm paraffin liver sections. The incubation was at 4° C. overnight. This antibody recognizes a 160 kD glycoprotein expressed by murine macrophages. Leenen et al. (1994) *J. Immunol. Methods* 174:5-19. This antigen is not expressed by lymphocytes or polymorphonuclear cells. To demonstrate specificity, rat IgG 2B (Pharmingen, San Diego, Calif.) was used as a negative control. Biotinylated rabbit anti-rat IgG was used as a secondary antibody. The antibody was detected using Vectastain Elite ABC reagent (Vector Labs, Burlingame, Calif.) followed by Metal Enhanced DAB (Pierce, Rockford, Ill.). The sections were counterstained with Mayer's hematoxylin.

Nude mice that have been intramuscularly injected with CHO cells were anesthetized by intraperitoneally injecting 100 µl Nembutal (Abbott Laboratories, Chicago, Ill.) and perfused with 10 ml of perfusion buffer (NaCl 142 mM, KCl 6.7 mM, HEPES 10 mM). After sacrificing the animals, the livers were removed and minced into fine pieces. Collagenase digestion of the tissue pieces was carried out at 37° C. for 30 min in digestion buffer (67 mM NaCl, 6.7 mM KCl, HEPES 100 mM, $CaCl_2$ 5 mM) supplemented with 50 µg/ml Liberase RH (Roche Molecular Biochemicals, Indianapolis, Ind.). Single cell suspensions were obtained after passing the digested liver suspension through a 70 µm cell strainer (Falcon, Bedford, Mass.). For BrdU staining, the in situ Cell Proliferation Kit was used according to the manufacturer's recommendations (Roche Molecular Biochemicals, Indianapolis, Ind.). In short, cells were washed, ethanol-fixed and the DNA denatured by HCl treatment. DNA-incorporated BrdU into was detected by staining with an anti-BrdU-FLUOS antibody (anti-BrdU-F(ab')$_2$-FITC conjugate). For flow cytometry, brightly autofluorescent monocytic cells were rejected from the analysis by forward/side scatter-gating. 10,000 gated cells were acquired and analyzed on a Becton Dickinson (San Jose, Calif.) FACSCalilbur flow cytometer.

For the detection of recombinant human VEGF protein in mouse serum samples, a fluorimetric anti-VEGF enzyme-linked immunosorbant assay (ELISA) was performed as described before. Rodriguez et al. (1998) *J. Immunol. Methods* 219:45-55. The limit of sensitivity of the assay in the presence of mouse serum was 200 pg/ml. The assay is specific for human VEGF and does not cross-react with murine VEGF.

For detection of recombinant human HGF, a previously described ELISA was used (Koch et al. (1996) *Arthr. Rheum.* 39: 1566-75), with some modifications. In brief, an anti-human HGF monoclonal antibody was used to coat 96-well microtiter plates. After a 1-hour incubation at room temperature, the wells were washed and serial dilutions of serum samples were added. rHGF was used as a reference standard. Following a 2-hour incubation and a wash, biotinylated sheep anti-HGF was added and incubated for 1 hour. After washing, horseradish peroxidase conjugated streptavidin (Amdex) was added and incubated for 30 minutes. After washing, the substrate solution, tetramethyl benzidine (Sigma), was added. Plates were read on a microtiter plate reader (Molecular Devices) at 450 nm with a subtracted blank at 650 nm. A four-parameter curve fitting program was used to generate a standard curve and sample concentrations were derived by interpolation in the standard curve range.

All animals were injected with BrdU (100 mg/kg) 1 hour prior to killing. Tissues were fixed in 10% neutral buffered formalin for 12 to 16 hours prior to paraffin embedding. H&E staining and immunohistochemistry for Flk-1 expression was performed as described previously (Gerber et al., 1999). Briefly, tissue sections were pretreated with Trilogy antigen retrieval solution (Cell Marque, Austin, Tex.) at 99° C. for 1 hr and then incubated with rat anti-mouse Flk-1 (mAb MALK-1, Genentech) at 3.9 mg/ml. overnight at 4° C. Immunoreactivities were visualized by the avidin-biotin complex technique using Vectastain Elite ABC kit (Vector Laboratories, Burlingame, Calif.) with diaminobenzidine as chromogen. Hematoxylin was used as counterstain. BrdU immunohistochemoistry was performed as previously described (Gerber et al., 1999).

Results

Transplant of CHO-VEGF Cells Results in Liver Growth in vivo

To study the effect of sustained levels of VEGF protein in mice, CHO-VEGF cells were injected intramuscularly into both legs of 3-4 week, 6-8 week or 12-14 week old beige nude mice. An identical number of CHO-DHFR cells, CHO-HAg cells, or CHO-HGF cells was injected into control animals. After two weeks, the serum concentrations of human VEGF in the CHO-VEGF animals were 3.3±1.7 ng/ml, (range 0.8-5.4 ng/ml). hVEGF was undetectable in the sera of CHO-DHFR and CHO-HAg control animals. The HGF levels in the serum of CHO-HGF animals were 1.25±0.87 ng/ml (range 0.50-2.00).

Figure 1A:
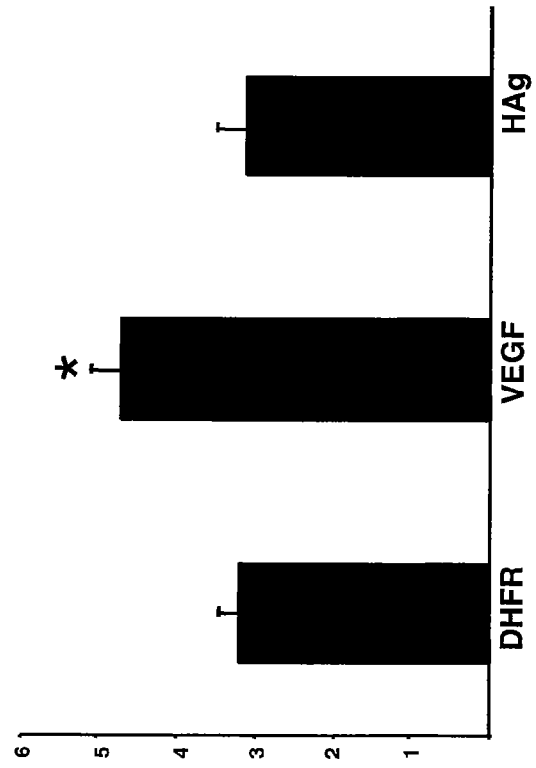
Figures 1C, 1D:
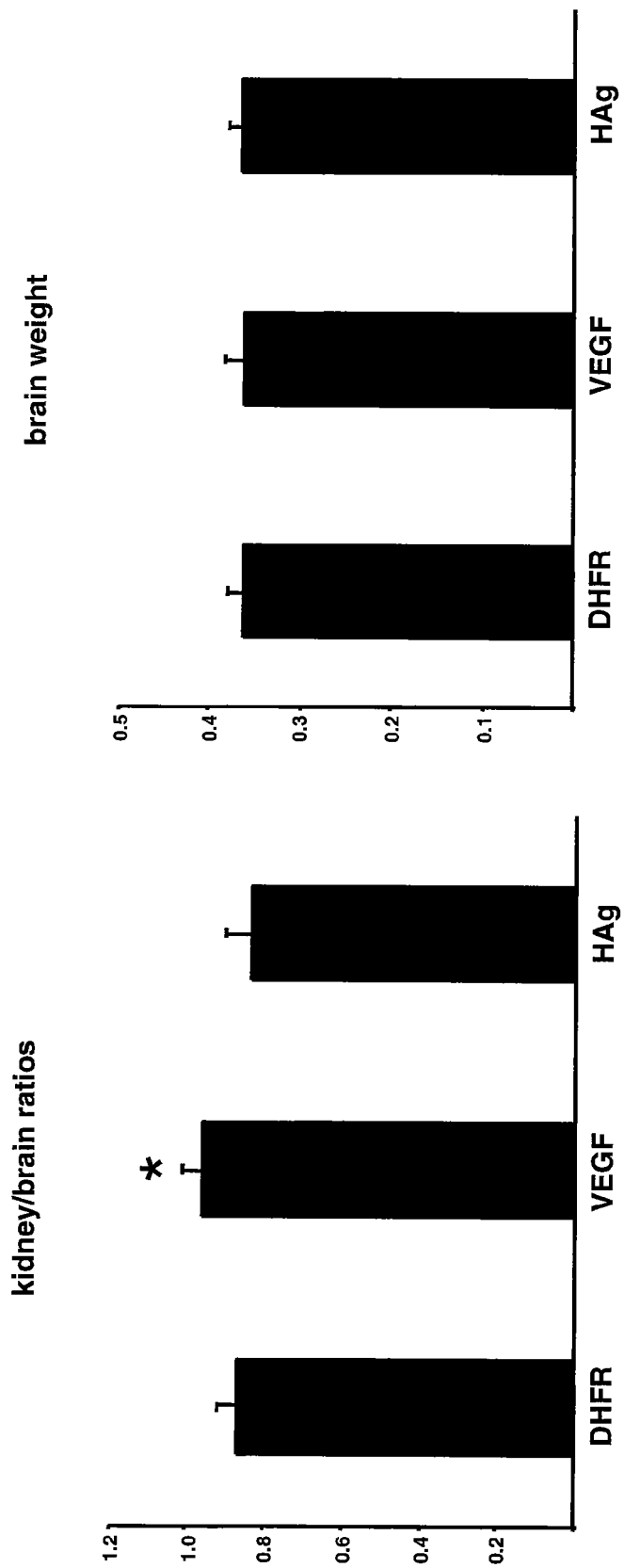

As shown in FIGS. 1A-1D, substantially increased liver sizes were observed in the CHO-VEGF groups. Very similar results were obtained in both age groups and therefore only data from the 3-4 week old group were shown. Since the brain weight remained unchanged within treatment groups (FIG. 1D), other organ weights were normalized to the constant brain weight. The liver/brain ratio, i.e. the relative liver mass, of the CHO-VEGF group (4.73±0.39) was highly significantly increased when compared to the CHO-DHFR (3.18±0.25, $p<0.0001$) and the CHO-HAg (3.00±0.45, $p<0.0001$) controls (FIGS. 1A, B). This reflects an increase of relative liver masses of 49 and 59%, respectively. The heart/brain ratio was also significantly increased in the CHO-VEGF group (0.376±0.052 compared to 0.304±0.022 and 0.304±0.017 in the CHO-DHFR and the CHO-HAg groups, respectively; CHO-VEGF versus CHO-DHFR, $p<0.05$). As well, the kidney/brain ratio (0.976±0.071 compared to 0.860±0.070, $p<0.05$ and 0.822±0.097, $p<0.02$ in the CHO-DHFR and the CHO-HAg groups) was significantly increased (FIG. 1C). These effects, however, were much less pronounced than the increases in liver size. The highly significant increases in the absolute and relative liver mass in the VEGF-treated animals were consistently observed in five independent experiments. Among those different experiments, the relative liver weight was increased 30-69% in the CHO-VEGF group when compared to the CHO-DHFR group. A further increase in liver mass was observed three weeks after implantation of CHO-VEGF cells, but this was frequently associated with signs of distress and mortality. Interestingly, no appreciable effect on liver growth was observed in the CHO-HGF group (FIG. 1B).

VEGF in Slow Release Preparation also Promotes Liver Growth

The above described effects were also reproduced by injecting a slow release formulation of highly purified human recombinant VEGF$_{165}$ protein. Mice were i.m. injected in the legs with VEGF-PLGA microspheres on days 1, 7, and 10. The dose of released VEGF protein was about 4.5 mg/kg/animal. As in the CHO-VEGF treated mice, the liver/brain ratio of the VEGF-PLGA injected mice was significantly increased (4.057±0.274, $p<0.05$, n=3) when compared to control animals (3.396±0.302, n=4) (FIG. 1E). Such increase in liver growth is less pronounced than that obtained with the CHO-VEGF cell transplant. However, the concentrations of human VEGF in the serum of VEGF-PLGA treated animals at the time of sacrifice were 200 pg/ml. This finding indicates that purified recombinant VEGF is also able to promote liver growth.

Systemic VEGF Results in a High Number of Mitotic Cells in the Liver

Standard histological analysis of the livers of CHO-VEGF injected animals revealed that a large number of hepatic cells displayed mitotic figures, as indicated by BrdU immunohistochemistry. Mitotic activity was seen in both parenchymal and non-parenchymal cells of CHO-VEGF treated livers. In livers of CHO-DHFR control animals, only 1 mitotic hepatocyte was seen in only 1 out of 5 animals in a total number of 10 high power (40×) fields examined. In contrast, 100% of the livers of the CHO-VEGF group showed at least 5 mitotic figures per 10 high power fields (range 5-11). Moreover, the proliferating hepatocyte compartment represented 6.44±0.96% (CHO-DHFR 1.02±0.74 and CHO-HGF 1.55±1.48%) as quantified by FACS analysis of hepatocytes isolated from BrdU-injected CHO-VEGF mice.

Since VEGF is known to be able to promote vascular permeability (Dvorak et al. (1995) *Am. J. Pathol.* 146:1029-39), the possibility exits that at least some of the increase in liver size is due to fluid retention, resulting in hepatocyte swelling. However, analysis of the area density of hepatocytes did not reveal any difference between CHO-DHFR and CHO-VEGF groups, indicating that hepatocyte mitogenesis fully accounts for the effect.

More Complex Branching of Sinusoid Endothelial Cells in the Liver Following VEGF Exposure Increased hepatocyte mitotic activity, sinusoidal cell hyperplasia and increased extramedullary hematopoietic activity were present in all animals injected with CHO-VEGF cells. However, no evidence of angioma or other abnormal vascular proliferation was detected in any specimen. The liver of animals injected with CHO-DHFR, CHO-HAg and CHO-HGF were within normal limits. Immunohistochemistry for Flk-1 around a terminal hepatic venule demonstrated a normal pattern of sinusoidal and non-sinusoidal endothelial staining in the liver of a CHO-DHFR animal. In the CHO-VEGF liver, the sinusoids appeared to have a more complex branching architecture and an apparent increased endothelial staining.

Example 3

Stimulation of Hepatocyte Mitogenesis

Methods

Hepatocytes were isolated from nude mice following retrograde liver perfusion, according to a previously described procedure. Harman et al. (1987) *J. Pharmacol. Methods* 17:157-63. The inferior vena cava was cannulated with a 22G Abbocath T catheter (Abbott Lab) and the portal vein was severed. The livers were perfused in situ with a 0.1% collagenase, 2 mM CaCl2 in PBS solution at a flow rate of 3 min/min for 10-15 minutes. Hepatocytes were seeded in 24-well plates at a density of $5 \times 10^4$ cells per well in William's E medium (GIBCO BRL) supplemented with 10% heat-inactivated fetal bovine serum (GIBCO BRL), 1 μg/ml insulin, 10 μg/ml transferrin, 1 μg/ml aprotinin (Sigma), 2 mM 1-glutamine, 100 U/ml penicillin and 100 μg/ml streptomycin (GIBCO BRL) and allowed to adhere overnight. The medium was then carefully removed from each well and medium containing growth factors (murine EGF, murine HGF, recombinant human VEGF, murine PlGF, VEGF-E, KDR$^{sel}$ or Flt-$^{sel}$) was added. After a 24-hour incubation, cells were pulsed with 1 μCi/well methyl-3H thymidine (47 Ci/mmol, Amersham Pharmacia Biotech), and incubated overnight. The following day, plates were harvested by rinsing in cold PBS followed by a 15 minute incubation in cold 10% TCA. Wells were subsequently rinsed with water and 200 μl of 0.2 N NaOH was added. This volume was then added to scintillation fluid and analyzed in a Beckman Liquid Scintillation System.

For trans-well cultures, $5 \times 10^4$ hepatocytes were placed in the upper chamber on a 0.4 μm pore size polyester membrane (Costar), and $1 \times 10^5$ LSEC were seeded in the lower chamber of the 24 well plate that was previously coated with a 0.002% solution of fibronectin (F1141, Sigma). Cells were allowed to adhere overnight. Media was removed and growth factors were added in CSC media (Cell Systems) supplemented with 0.2% FCS and 0.1% BSA. After a 24-hour incubation, cells were pulsed with 1 µCi/well methyl-$^3$H thymidine and incubated overnight. Incorporated counts were assessed as described above.

Sinusoidal endothelial cells were isolated from nude or C57B16 mice. Following retrograde perfusion as above described, the liver was removed, minced and parenchymal cells were depleted following 2 low-speed centrifugations. The remaining non-parenchymal cells were incubated with endothelial cell-specific anti-CD31 antibody conjugated to biotin (Pharmingen MEC13.3) in PBS, 2 mM EDTA and 0.5% BSA, on ice for 5-10 minutes, washed, and then incubated with 25 µl of streptavidin-conjugated magnetic microbeads (Milteny biotech). The streptavidin-decorated endothelial cells were then captured on LS+/VS+ columns placed in the magnetic field of a Vairo MACS separator (Milteny biotech). Cells were washed and then eluted by removing the column from the magnetic field. The identity and purity of endothelial cells was verified by FACS analysis for CD31, CD34 (Pharmingen) and Flk-1 (Genentech), and uptake of DiI-labeled Ac-LDL (Biomedical Technologies Inc., Stoughton, Mass.). The purified endothelial cells were plated in 6-well or 24-well dishes previously coated with a 0.002% solution of fibronectin in CSC-medium with serum and growth factors (Cell Systems), supplemented with an additional 5 ng/ml recombinant human VEGF.

Primary LSEC passage 1 were plated at a density of 1×10$^6$/well in 6-well plates. After an overnight incubation cells were starved in CSC media containing 0.2% FCS, 0.1% BSA for 12-18 h. Media was changed to CSC media containing 0.1% BSA for 90 minutes and then factors (20 ng/ml) were added for a 5 minute incubation. Samples were quickly rinsed in cold PBS and lysed in 0.8 ml RIPA buffer (150 mm NaCl, 1% Nonidet P-40, 0.5% sodium orthovanadate, 50 mM Tris pH8.0) containing a protease inhibitor mixture (Roche MB 1836145) and phosphatase inhibitor cocktail (Sigma). Anti-phospho-ERK antiserum was purchased from Cell Signaling Technology and pan-ERK antiserum, from Signal Transduction Laboratories.

Results

VEGF is not a Mitogen for Hepatocytes

Figure 2A:
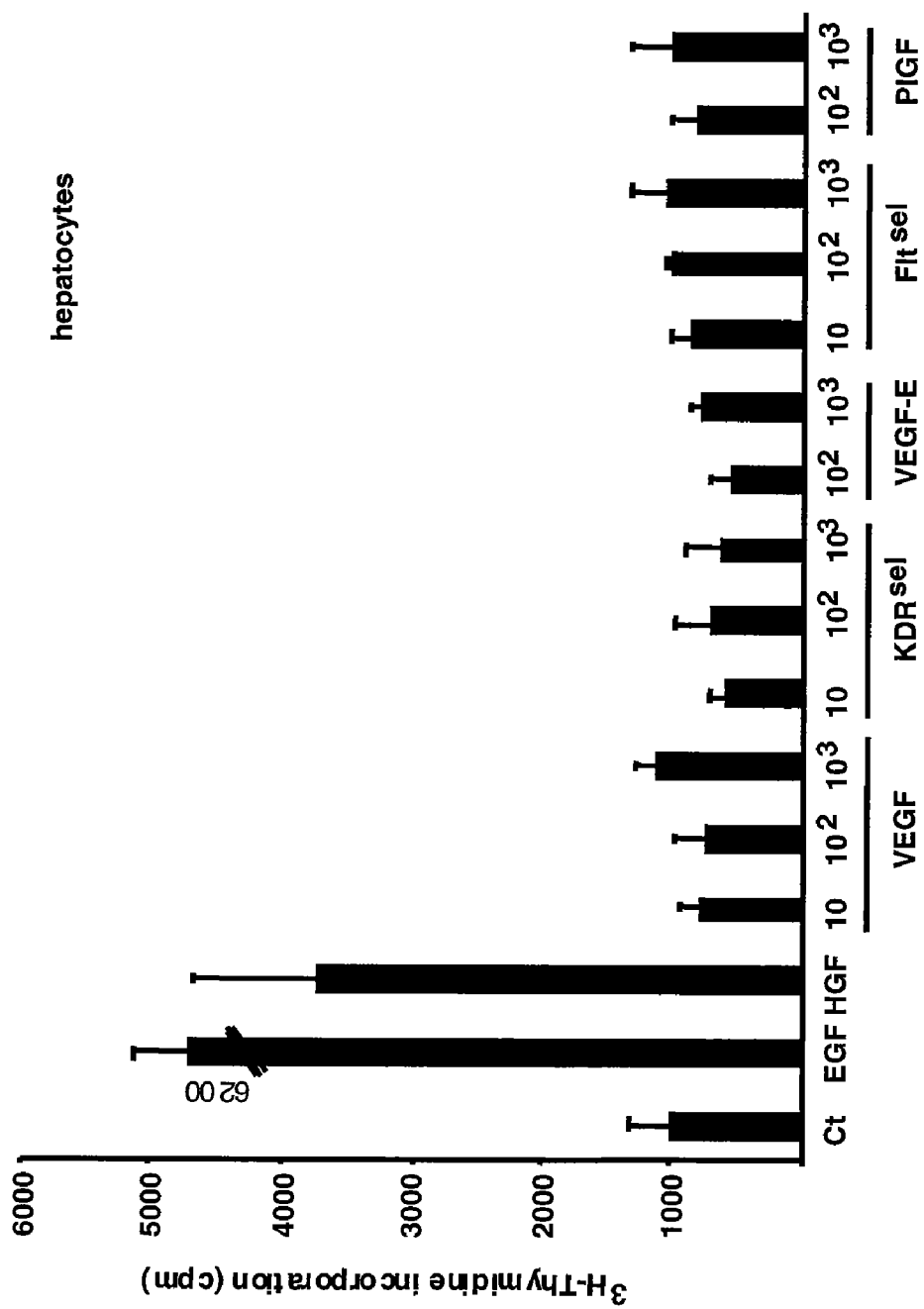
FIGS. 2A-2D depict effects of various protein agents on cultured hepatocytes or LSECs, either alone (2A, 2B) or in a transwell setting (2C, 2D). 2A: Effects of EGF, HGF, VEGF, or VEGFR-selective agonists on $^3$H-thymidine incorporation in primary hepatocytes when cultured alone. EGF (10 ng/ml) and HGF (50 ng/ml) stimulated $^3$H-thymidine uptake, while VEGF, $KDR^{sel}$, VEGF-E, $Flt^{sel}$ and PIGF, tested at the indicated concentrations (ng/ml), failed to induce $^3$H-thymidine uptake in hepatocytes. 2B: Wild type VEGF and the KDR agonists $KDR^{sel}$ and VEGF-E induced $^3$H-thymidine uptake in primary cultures of LSEC. In contrast, the Flt-1 selective agonists, $Flt^{sel}$ and PIGF, failed to promote LSEC proliferation. Ligands were added at the concentration of 10 ng/ml, except for HGF, which was given at 50 ng/ml. 2C: In transwell LSEC/hepatocytes co-cultures, VEGF, $KDR^{sel}$ and VEGF-E induced $^3$H-thymidine incorporation in LSEC, whereas the Flt-1 agonists are ineffective. The concentration of ligands is the same as in 2B. 2D: In transwell LSEC/hepatocytes co-cultures, PIGF or $Flt^{sel}$ induced H-thymidine incorporation in primary hepatocytes to a level comparable to HGF-treated cells. In contrast, incubation with $KDR^{sel}$ or VEGF-E resulted in little or no stimulation of hepatocyte proliferation. The concentration of ligands is the same as in 2B. Error bars represent standard deviation.

VEGF has been characterized as a mitogen with a target selectivity largely restricted to vascular endothelial cells (Conn et al., 1990; Ferrara and Henzel, 1989; Plouet et al., 1989). However, recent studies have reported mitogenic effects of VEGF also on certain non-endothelial cell types, including retinal pigment epithelial cells (Guerrin et al., 1995), and Schwann cells (Sondell et al., 1999). Therefore, it was important to test whether VEGF has any direct mitogenic effect on hepatocytes. As illustrated in FIG. 2A, in freshly isolated mouse hepatocytes, VEGF tested over a broad concentration range failed to induce any increase in $^3$H-thymidine incorporation. Likewise, neither the VEGFR-selective VEGF variants Fltsel and KDRsel, nor the naturally occurring VEGFR-selective agonists PlGF (for VEGFR-1) and VEGF-E (for VEGFR-2) induced hepatocyte proliferation. In contrast, HGF induced a dose-dependent stimulation, with a maximal increase at ~50 ng/ml. EGF, tested at the concentration of 10 ng/ml, also induced a significant increase in $^3$H-thymidine uptake. This is consistent with in situ ligand binding studies showing that VEGF binding sites are localized to endothelial cells, but not hepatocytes, in liver sections. Jakeman et al. (1992) *J. Clin. Invest.* 89:244. Thus, the hepatocyte growth-promoting effects of VEGF require the action of endothelial cell-derived paracrine mediator(s).

Co-culture of Hepatocytes with Sinusoidal Endothelial Cells

To further probe the molecular mechanism of the hepatocyte mitosis, cultures of primary hepatocytes and primary sinusoidal endothelial cells (LSEC) were established either in isolation or in a co-culture system in a trans-well format.

Figure 2B:
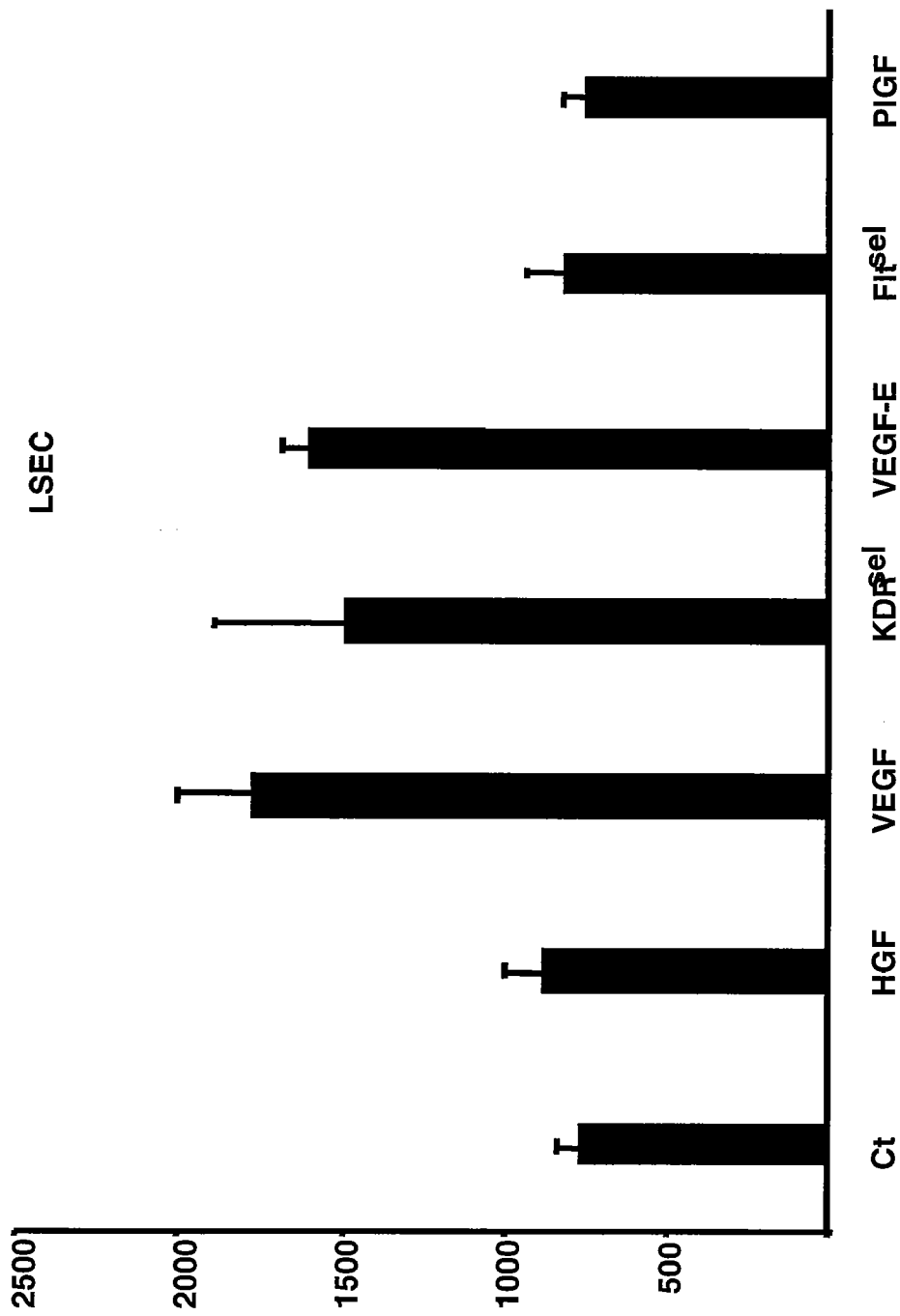
Figures 2C, 2D:
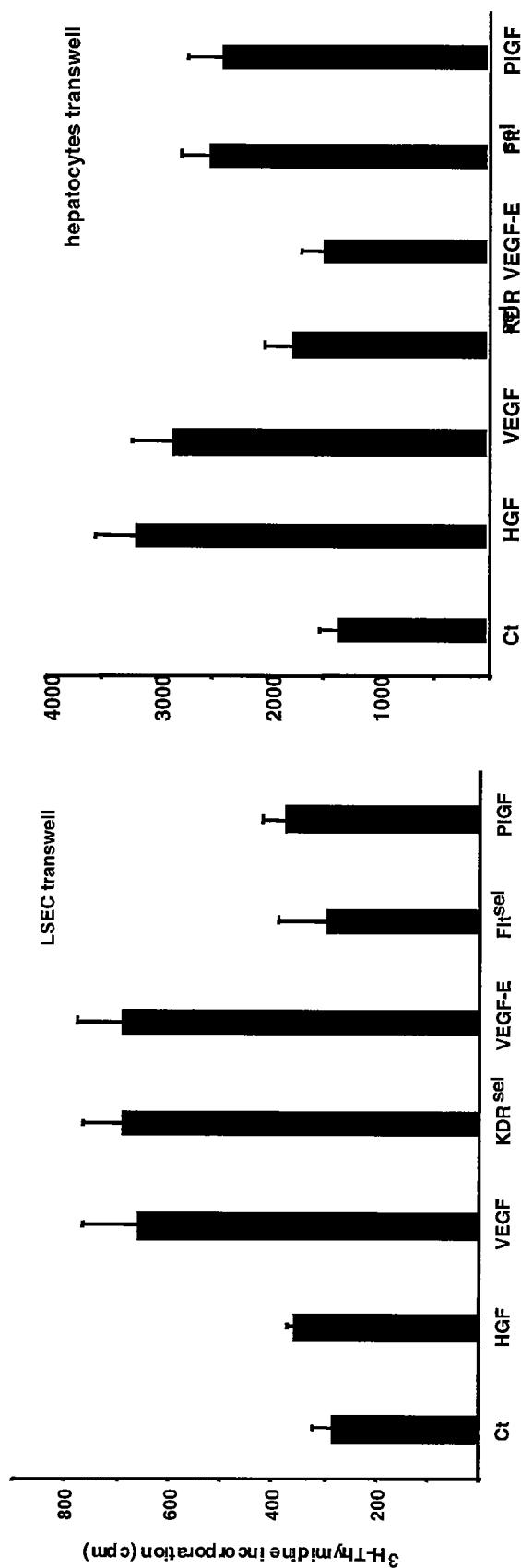
Figure 3:
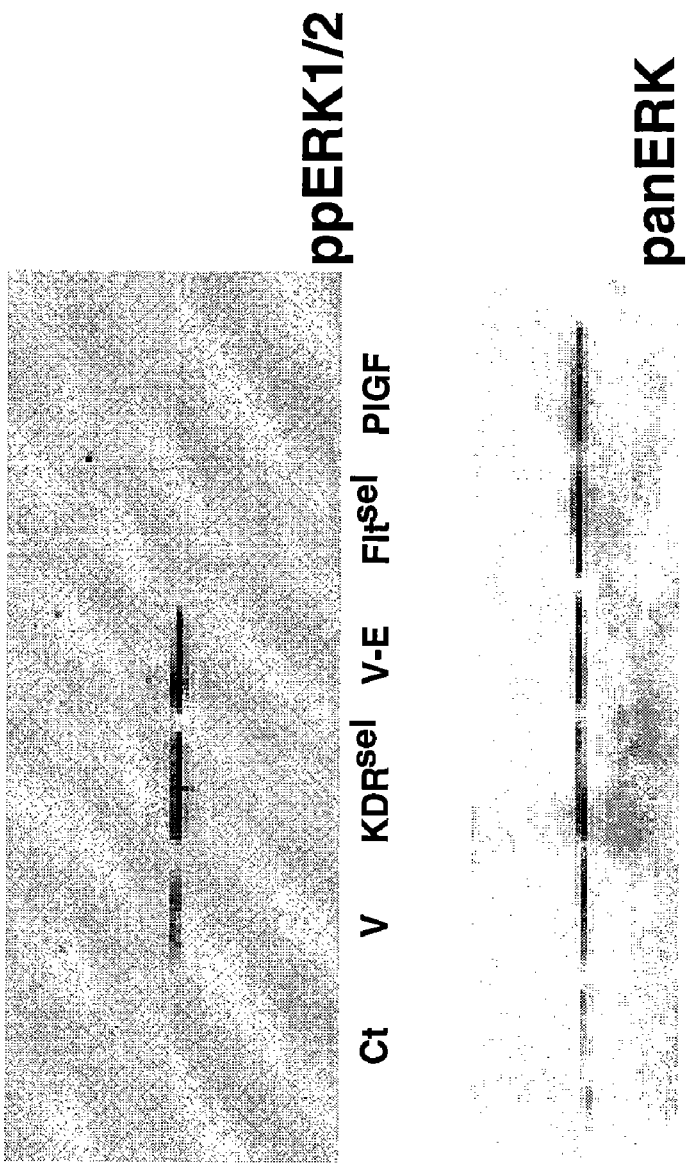
FIG. 3 depicts effects of VEGF and VEGFR selective agonists on MAP kinase activation in sel LSEC. The ability of wild type VEGF (V) and $KDR^{sel}$ and VEGF-E (V-E) to induce ERK activation is shown in the upper panel representing an immunoblot for phosphorylated ERK1/2. $Flt^{sel}$ and PIGF failed to induce ERK phosphorylation although comparable levels of ERK1/2 were present as indicated in the panERK immunoblot in the lower panel. All ligands were added at 20 ng/ml.

In both isolated and trans-well co-cultures, VEGF, KDR$^{sel}$ and VEGF-E induced a 2-2.4-fold increase in $^3$H-thymidine incorporation in primary LSEC cultures (FIGS. 2B and 2C), and a robust activation of ERK1/2 phosphorylation as assessed with the phospho-specific antibody (FIG. 3, upper panel). In contrast, Flt$^{sel}$ or PlGF were indistinguishable from negative control in LSEC proliferation (FIGS. 2B and 2C) and ERK1/2 phosphorylation (FIG. 3, upper panel). HGF had little effect on LSEC proliferation (FIG. 2B). This is in agreement with previous studies showing that HGF is a more potent mitogen for hepatocytes compared to nonparenchymal cells such as LSEC (Patijn et al. (1998) *Hepatol.* 28:707-16), although in other biological contexts HGF is highly effective endothelial cell mitogen (Rosen and Goldberg (1997) Rosen, E, Goldberg, ID, Eds. Springer Verlag. pp. 193-208).

However, in the trans-well format, wt-VEGF, Flt$^{sel}$, or PlGF, resulted in hepatocyte proliferation comparable to that induced by recombinant mHGF (FIG. 2D). Since these molecules are devoid of direct mitogenic effects on hepatocytes (FIG. 2A), these findings indicate that LSEC are stimulated to release paracrine factors in response to these ligands. Neither KDR$^{sel}$ nor VEGF-E resulted in any significant hepatocyte stimulation, indicating that VEGFR-2 activation is less efficient at triggering such paracrine effects, at least in LSEC (FIG. 2D).

HGF is a key hepatocyte mitogen and in initial experiments, strong upregulation of HGF mRNA expression were seen by in situ hybridization within the sinusoidal endothelium of mice implanted with CHO-VEGF relative to controls. Thus, HGF was tested as one of the potential paracrine mediators of the VEGF effect in LSEC-hepatocyte co-cultures. Addition of a polyclonal antibody raised against human HGF, which was able to achieve a ~50% neutralization of the activity of 50 ng/ml recombinant murine HGF at the concentration of 50 µg/ml, significantly inhibited the increase in $^3$H-thymidine incorporation induced by VEGF (30±2%), Flt$^{sel}$ (29±2.4%) or PlGF (30±1.3%) in the co-culture system. This less than complete inhibition likely reflects not only the partial HGF-neutralization, but also the presence of additional paracrine factors produced by LSEC.

Example 4

Differential Induction of Hepatotrophic Genes

To further define the factors induced within the endothelium, potentially contributing to the paracrine effects as previously described, the levels of RNA transcripts for a number of cytokines and receptors were examined in primary LSEC. Confluent primary endothelial cell cultures were dissociated by exposure to trypsin and seeded in 6-well plates at the density of 2×10$^6$ cells/well in growth factor-free CSC medium with 2.5% FBS. After 10-12 hours, media were changed and cells were incubated for 24 hours with recombinant factor, including rhVEGF, KDR$^{sel}$, Flt$^{sel}$, mPlGF and VEGF-E, all at 10 ng/ml. Cells were washed twice in ice cold PBS and total RNA was isolated using the RNeasy kit (Qiagen) according to the instructions of the manufacturer. Fifty ng of total RNA per reaction were analyzed using the RT-PCR kit from Perkin-Elmer, following the manufacturer's instructions (PE Applied Biosystems, Foster City, Calif.). Reactions were run in 96-well plates in a Model 7700

Sequence Detector (PE Applied Biosystems), and results were analyzed using Sequence Detection Software (PE Applied Biosystems). RT-PCR conditions were 30 min at 48°, 10 min at 95° C., and 40 cycles of 30 s at 95° C. and 90 s at 58° C. Data were normalized to GAPDH level, and total liver RNA was used to generate all standard curves. Each sample was analyzed in duplicate and the experiments were replicated twice for the full set of genes, or five times for HGF.

Primers and probes used were as follows:

TGFα, TGFβ, aFGF, bFGF, PlGF, Flt-1, Flk-1, and c-Met. Most striking was the reproducible and specific 5.5±2.3-fold induction of HGF in the VEGF and Flt-selective VEGF treated cultures, indicating that HGF is a target gene for Flt-1 mediated signaling events. IL-6 also appeared to be a selective target of Flt-1 signaling, induced 3.3±0.6-fold above non-treated LSEC cultures. HB-EGF and CTGF were induced to equivalent levels by VEGF, Flt$^{sel}$ or KDR$^{sel}$, and therefore may represent overlapping targets of VEGFR-1 and

TABLE 2

| Gene | Forward | Reverse | Probe |
|---|---|---|---|
| mGAPDH | 5'ATG TTC CAG TAT GAC TCC ACT CAC G (SEQ ID NO. 1) | 5'GAA GAC ACC AGT AGA CTC CAC GAC A (SEQ ID NO. 2) | FAM-AAG CCC ATC ACC ATC TTC CAG GAG CGA GA-TAMARA (SEQ ID NO. 3) |
| HGF | GGC AAG GTG ACT TTG AAT GA (SEQ ID NO. 4) | CAC ATG GTC CTG ATC CAA TC (SEQ ID NO. 5) | FAM-TTT CAG CCC CAG CAC ATA ACT CAG A-TAMARA (SEQ ID NO. 6) |
| HB-EGF | TGC TGC CGT CGG TGA TG (SEQ ID NO. 7) | ACC GGT CAC CAA CGC G (SEQ ID NO. 8) | FAM-TGA AGC TCT TTC TGG CCG CAG TGT TG-BHQ (SEQ ID NO. 9) |
| IL-6 | TCC TAC CCC AAT TTC CAA TGC (SEQ ID NO. 10) | TGA ATT GGA TGG TCT TGG TCC (SEQ ID NO. 11) | FAM-AAC AGA TAA GCT GGA GTC ACA GAA GGA GTG GCT A-BHQ (SEQ ID NO. 12) |
| CTGF | TTG GCC CAG ACC CAA CTA TG (SEQ ID NO. 13) | GGC GCT CCA CTC TGT GGT (SEQ ID NO. 14) | FAM-TGC GAG CCA ACT GCC TGG TCC-BHQ (SEQ ID NO. 15) |
| TGF | ACC CTG GTG GTA TAC TGA GAC A (SEQ ID NO. 16) | GGG GTC TCC CAA GGA AAG (SEQ ID NO. 17) | FAM-TGT CAG AGC CTC ACC GCG ACT C-TAMARA (SEQ ID NO. 18) |
| aFGF | TGA CGA CTT TTC TGG ATG GA (SEQ ID NO. 19) | ACA AGG AGG CTA CTG AGA AAG G (SEQ ID NO. 20) | FAM-AGT TTC CAT TCA CCA TTA GGA GGG AGT-BHQ (SEQ ID NO. 21) |
| bFGF | CCT CTC AGA GAC CTA CGT TCA A (SEQ ID NO. 22) | GGA GGT CAA GGC CAC AAT (SEQ ID NO. 23) | FAM-CGG TCC AGG TCT TCC ACC AAC TG-TAMARA (SEQ ID NO. 24) |
| PlGF | GCA GTA GCC CGT GGA CTT (SEQ ID NO. 25) | CGG TCC AGG TCT TCC ACC AAC TG (SEQ ID NO. 26) | FAM-ACA CAC AAC CCA GAC TTG TAT CGG TCA-TAMARA (SEQ ID NO. 27) |
| Flt-1 | GTC AAC GGC TGC CCT ATG AT (SEQ ID NO. 28) | CCG AGC GAT TTG CCT AGT TT (SEQ ID NO. 29) | FAM-TCT CTC CCG TGC AAA CTC CCA CTT G-BHQ (SEQ ID NO. 30) |
| Flk-1 | TCA TTA TCC TCG TCG GCA CTG (SEQ ID NO. 31) | CCT TCA TTG GCC CGC TTA A (SEQ ID NO. 32) | FAM-TTC TGG CTC CTT CTT GTC ATT GTC CTA CGG-BHQ (SEQ ID NO. 33) |
| c-Met | GCC CTT TCC AGA GAC TTG TT (SEQ ID NO. 34) | CAT CTC ACT GGC CTG TTC TC (SEQ ID NO. 35) | FAM-CCT ATG GAC TAC CAC TGC CTA GGG GA-TAMARA (SEQ ID NO. 36) |

Figure 4:
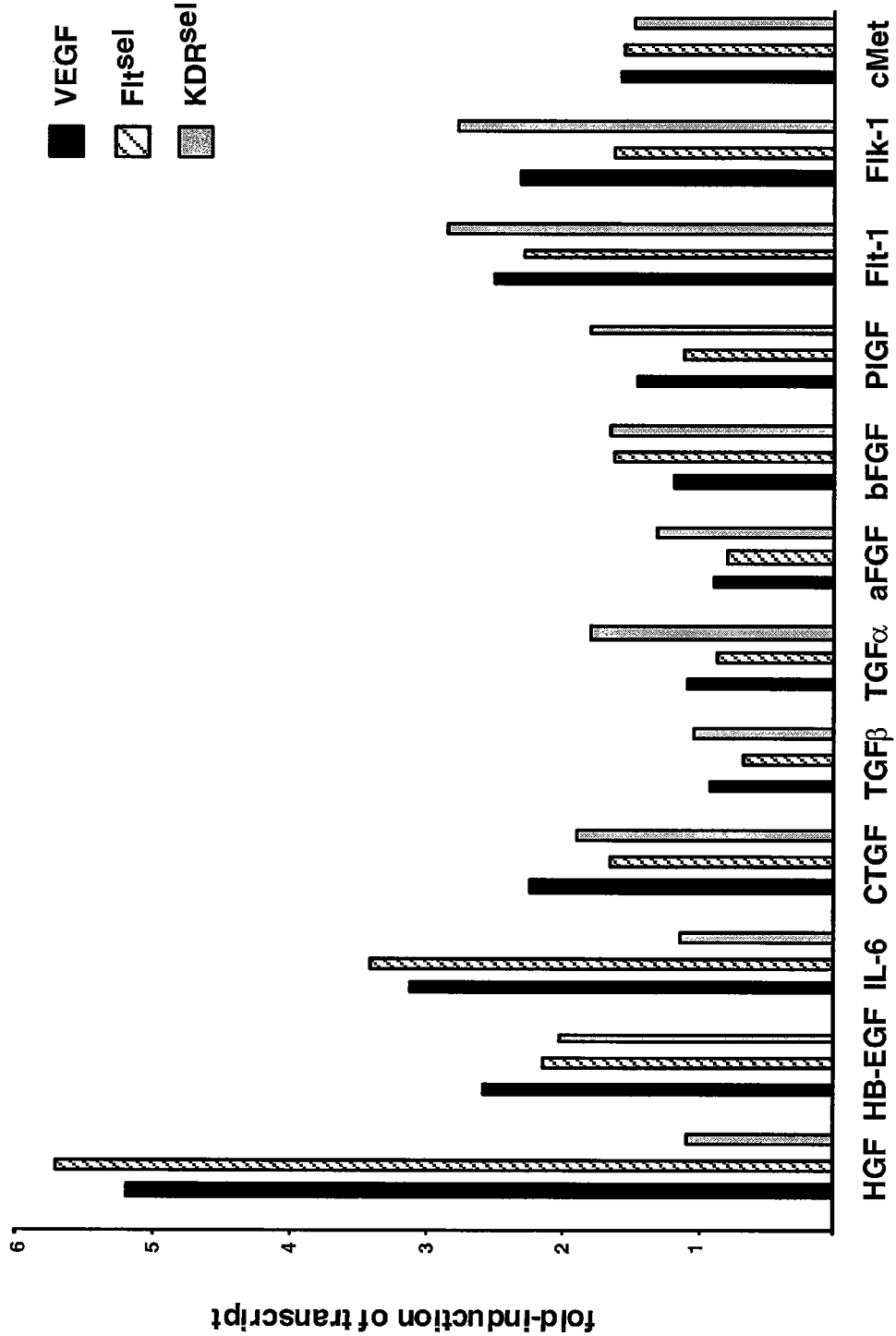
FIG. 4 shows that Flt-1 and KDR selective agonists induce expression of distinct and overlapping genes in LSEC. A representative experiment of Taqman analyses of 12 distinct gene transcripts in LSEC treated for 24 hours with 10 ng/ml VEGF, $KDR^{sel}$ or $Flt^{sel}$ and normalized to control, untreated cells arbitrarily set to the value 1. Expression profiles indicate that HGF and IL-6 induction by VEGF is selectively mediated by Flt-1, whereas expression of HB-EGF or CTGF is responsive to both Flt-1 and KDR mediated signals. TGFα and PIGF appear to be more responsive to KDR activation. See legend in upper right corner for bar graph coding.

FIG. 4 shows differential induction of hepatotrophic genes by VEGF or VEGFR selective agonists. The panel of potential gene targets analyzed included HGF, heparin-binding EGF (HB-EGF), IL-6, connective tissue growth factor (CTGF), VEGFR-2 signals. In two independent experiments, TGFα, PlGF and Flk-1 were higher in KDR$^{sel}$ treated cultures. These genes may therefore represent VEGFR-2 responsive targets. Although the expression levels of other transcripts including TGFα, acidic and basic FGF were not increased by any of the treatments, the levels of these transcripts were substantial in the cultured LSEC (i.e. Taqman threshold concentration values less than 23).

Example 5

Gene Delivery of VEGFR Agonists

To confirm that the effects of VEGF upon liver growth were not dependent upon the mode and/or site of production of VEGF, and to further explore the mechanism of VEGF activity, adenoviral vectors were used to introduce wt-VEGF (Av-VEGF) or receptor-selective agonists (Av-KDR$^{sel}$ or Av-Flt$^{sel}$) (Gille et al., 2001). The liver represents the major organ responsible for blood clearance of Adenovirus and is a natural site of infection via the IV route of administration.

Ad-VEGF, Av-Flt$^{sel}$ and Av-KDR$^{sel}$ and Ad-lacZ were generated using the AdEasy adenoviral vector system (Stratagene) essentially as described by the manufacturer. The coding regions were cloned between the NotI and HindIII sites of the pShuttleCMV vector. These vectors, along with the supplied pShuttleCMV-lacZ, were recombined, in BJ5183 electrocompetent bacteria (Stratagene), with the AdEasy vector containing the Ad5 genome deleted for E1 and E3 regions. Primary viral stocks were prepared by transiently transfecting the recombined AdEasy plasmids into host HEK293 cells. Adenovirus stocks were further amplified in HEK293 cells and purified using the Virakit Adeno purification kit (Virapur; Carlsbad, Calif.). Adenovirus titers were obtained by agarose-overlayed plaque assays.

Adenovirus was directly injected into the tail vein of mice. Virus was stored in Kit Formulation Buffer supplied by Virapur and the appropriate dilutions were made with PBS. The volume of virus and PBS injected was 100 µl for each animal. Doses of virus administered were as follows: Av-VEGF $10^7$, Av-LacZ $5\times10^8$, Av-Flt$^{sel}$ $5\times10^8$ and Av-KDR$^{sel}$ $5\times10^8$. Serum was collected when experiments were terminated, 7 or 14 days with virus alone, and 6 or 10 days for the CCl$_4$ experiments described below. One hour prior to sacrifice, all animals were intraperitoneally injected with 100 mg/kg bromodeoxyuridine (BrdU) (Sigma, St. Louis, Mo.). Livers, kidneys, heart, legs, and brains were removed and weighed. The collected tissues were immersed in formalin for histological evaluation. Statistical analysis was performed by ANOVA.

Within one week following injection of Av-VEGF, the liver mass increased by an average of 33.5+/−18.1% (from 23-54%). A clear angiogenic response was seen at a dose as low as of $10^7$ pfu. However, even small increments in the dose of Av-VEGF above $10^7$ were not well-tolerated and were associated with toxicity and in many cases morbidity by day 4 post-injection.

In addition to Av-VEGF, Adenovirus encoding KDR$^{sel}$ or Flt$^{sel}$ were also used for animal injections. Delivery of each adenovirus resulted in comparable levels of recombinant proteins. Seven days after delivery of $10^8$ pfu, plasma concentrations of KDR$^{sel}$ and Flt$^{sel}$ were respectively 15±8 and 31±18 ng/ml (n=6). The Av-KDR$^{sel}$ virus elicited a 22.3±7.6% (range 15-30%) increase in liver mass within one week. Although the increase in mass was of lesser magnitude, the morphological changes induced by Av-KDR$^{sel}$ were qualitatively indistinguishable from those induced by Av-VEGF and were characterized by hyperplasia of endothelium lining large vessels and sinusoids, with focal sinusoidal dilatation. In addition, there was reduplication of hepatocyte plates, an indicator of recent hepatocyte regenerative activity, and in the Av-VEGF group, there was some extramedullary hematopoiesis. Av-Flt$^{sel}$ VEGF resulted in a small but reproducible (average 5%) increase in liver mass. However, there was no evidence of angiogenesis in these animals as determined by histological evaluation. Therefore, although the Flt$^{sel}$ was able to stimulate hepatocyte proliferation in vitro, without an accompanying increase in the vascular compartment in vivo, the overall organ growth was substantially attenuated or constrained, indicating that stimulation of angiogenesis may be necessary for maximal growth of adult liver. No liver growth was associated with tail vein injection of the control virus, Av-LacZ, at any of the doses tested (up to $10^9$ pfu) and the liver histology was essentially normal.

Figures 5A, 5B:
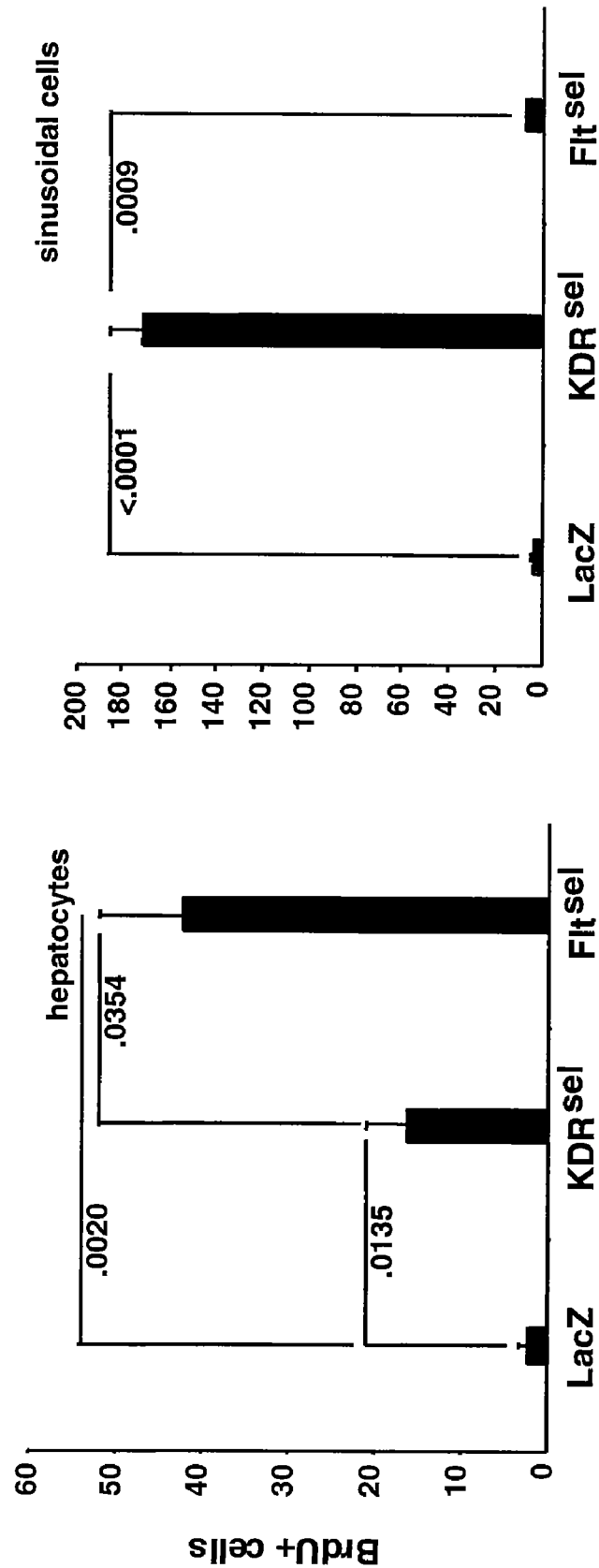
FIGS. 5A and 5B depict in vivo proliferation of hepatocytes versus sinusoidal endothelial cells in response to selective VEGFR activation. Quantitative analysis of proliferating hepatocytes (5A) and sinusoidal cells (5B) was performed after BrdU immunohistochemistry of liver sections from animals treated with Av-LacZ, AV-KDR$^{sel}$, or AV-Flt$^{sel}$ 10 days after AV administration. Values are means±SEM. Level of significance was assessed by unpaired t tests; P values are indicated.

To further investigate the underlying mechanism of liver growth, proliferating cells were counted by assessing bromodeoxyuridine (BrdU) immunohistochemistry, in liver sections 10 days after Av-KDR$^{sel}$ or Av-Flt$^{sel}$ delivery. As shown in FIGS. 5A and 5B, Av-Flt$^{sel}$ promoted a significant sel increase in hepatocyte proliferation compared with Av-KDR and Av-LacZ (FIG. 5A). Conversely, Av-KDR$^{sel}$ induced the greatest proliferation of sinusoidal cells (FIG. 5B). The Av-Fltsel-treated livers showed few proliferating sinusoidal cells and in this respect were almost indistinguishable from the Av-LacZ controls (FIG. 5B).

Example 6

Protection Against Liver Damage

In initial liver protection experiments, adult nude mice were implanted with CHO-DHFR or CHO-VEGF cells as above described. After ten days, both groups were subdivided into two subgroups (n=7) according to the materials the animals receive: vehicle (olive oil) or the potent hepatotoxic agent carbon tetrachloride CCl$_4$. Both vehicle and CCl$_4$ were given at 4 ml/kg by oral gauvage. After 48 hours, animals were killed, blood was collected and tissues were harvested and fixed as above described. Five µm paraffin sections were obtained from formalin fixed livers of CCl$_4$-treated CHO-DHFR (n=7) and CHO-VEGF (n=7) animals. The sections were stained with Gil's Hematoxylin only and coverslipped before conducting a blinded analysis. A Hamamatsu Digital Camera attached to a Nikon Eclipse TE300 microscope captured bright field images and total tissue area and necrotic area for each sample were measured using MetaMorph imaging software (Universal Imaging Corp, West Chester, Pa.). Total tissue area was defined as the total area of the section analyzed minus the area of the vascular lumens and was approximately 20 mm in each sample analyzed. The data is expressed as the ratio of necrotic area to total tissue area+/−SE.

The CHO-DHFR animals exhibited features typical of CCl$_4$ toxicity, with extensive necrosis of hepatocytes around terminal hepatic venules. In CHO-VEGF animals, the extent of necrosis was substantially reduced. Serum levels of alanine aminotransferase (ALT) and aspartate aminotranferase (AST), which are key indicators of the extent of liver damage, were reduced respectively 85.3% and 66.3% in the CHO-VEGF group relative to CHO-DHFR (Table 3).

TABLE 3

Protective Effects of VEGF and VEGFR-selective Variants in the $CCl_4$ Acute Liver Toxicity Model

| Experiment | Group | % reduction in serum ALT[a] | % reduction in serum AST[a] |
|---|---|---|---|
| I | CHO-VEGF | 85.4 | 66.3 |
| II[b] | Av-VEGF | 36.5 | 37.9 |
|  | Av-KDR$^{sel}$ | 44.5 | 59.5 |
|  | Av-Flt$^{sel}$ | 65.0 | 78.7 |
| III[b] | Av-VEGF | −36.6 | −19.3 |
|  | Av-KDR$^{sel}$ | 86.1 | 86.5 |
|  | Av-Flt$^{sel}$ | 70.3 | 68.3 |

[a]The % reduction is relative to control group for each experiment. For I, CHO-DHFR served as control, for II and III, Av-LacZ served as control group.
[b]Adenovirus was administered 4 days prior to $CCl_4$ treatment in II, and 8 days prior to $CCl_4$ in experiment III. Each group consisted of at least 6 mice.

The $CCl_4$ experiments were replicated in the Adenovirus-treated mice in several studies. Adenoviral vector construction and transfection are described above. The Adenovirus was given 4 or 8 days prior to $CCl_4$ administration. In Av-VEGF treated livers, ALT levels were reduced an average 36.5% in one experiment, relative to Av-LacZ. However, it was difficult to reproduce such finding and in one experiment ALT levels in the Av-VEGF group treated with $CCl_4$ levels were even higher than in the Av-LacZ group. In this case, VEGF delivery was associated with profound vascular changes, with extensive sinusoidal dilatation and accompanied by high mortality. These and other related experiments seem to suggest that although Av-delivered wild-type VEGF is capable of providing a protective mechanism to hepatocytes, the very narrow dose response, resulting in toxicity or lack of effects with small changes in virus titer, indicates an unattractive, narrow therapeutic window, at least when VEGF is delivered by this modality.

In light of the differential responses observed in vitro, further studies were conducted to examine the abilities of Av-KDR$^{sel}$ or Av-Flt$^{sel}$ to rescue liver functions in $CCl_4$ treated mice. When Av-KDR$^{sel}$ was administered 4 days prior the $CCl_4$, ALT levels were reduced approximately 45% compared to Av-LacZ (Table 3). The protective effect was greater when Av-KDR$^{sel}$ was delivered 8 days before the toxic injury, approaching 85% reduction in transaminase levels. Animals in the Av-Flt$^{sel}$ groups also exhibited a marked protection and approximately 64% reduction in serum ALT levels relative to AvLacZ groups treated with $CCl_4$. No significant difference was observed whether Av-Flt$^{sel}$ was administered 4 or 8 days before $CCl_4$ (Table 3).

The morphology study of livers in the group that received Adenoviral vectors 8 days before $CCl_4$ revealed that there was extensive confluent perivenular necrosis in Av-LacZ, involving 30-50% of the total hepatocyte mass. In Av-KDR$^{sel}$ animals, perivenular hepatocyte necrosis was much less severe, ranging from single cell necrosis to limited areas of confluent necrosis. Peri-portal areas showed changes similar to those animals that had not received $CCl_4$. Av-Flt$^{sel}$ animals had a similar reduction in hepatocyte necrosis and showed a moderate, mixed inflammatory cell infiltrate around terminal hepatic venules and mild endothelial cell hyperplasia. Endothelial cell changes were much less striking than in the KDR$^{sel}$ group.

Thus, although Av-Flt$^{sel}$ did not induce endothelial cell proliferation or a substantial increase in liver mass in adult animals, it was essentially as effective as KDR$^{sel}$ in preserving liver function during acute liver damage. Furthermore, Av-Flt$^{sel}$ displayed no apparent toxicities even when the virus was administered at a dose of $10^9$ with animals monitored over a 14 day period.

The liver toxicity studies with $CCl_4$ confirmed the marked differences in the mode of action of KDR$^{sel}$ and Flt$^{sel}$. Although delivery of both molecules resulted in a comparable degree of liver salvage, the lesions appeared strikingly different morphologically, consistent with different protective mechanisms. Interestingly, KDR$^{sel}$ protection showed a time-dependence, with greater protection when the virus was delivered 8 days before the toxic injury. This is consistent with the hypothesis that the KDR$^{sel}$ protective effects primarily depend on endothelial proliferation, which may amplify a paracrine survival-factor cascade. In contrast, Flt$^{sel}$ was equally effective at both time points, consistent with a protective mechanism based on the release of survival/mitogenic factors from nonproliferating LSECs, with much reduced or absent dependence on angiogenesis and the release of survival factors from non-proliferating LSEC.

The Adenovirus studies also suggest that Av-delivered VEGF, although able to induce potently angiogenesis and liver growth, proved to have a very tight dose-response/toxicity such that it resulted in either a modest salvage of liver function or in frankly detrimental affects with only marginal changes in the virus titer. Doses 2-4 fold lower had no effect, whereas, doses 2-4 fold higher, were associated with toxicity and morbidity. The systemic toxicity and tight dose response of VEGF have been previously noted (Thurston et al. (2000) Nat. Med. 6:460-63; Wong et al. (2001) Proc. Natl. Acad. Sci. USA 98:7481-6).

Although Av-KDR$^{sel}$ was toxic when given at the highest doses ($10^9$), it showed a better safety profile than VEGF, and even plasma concentrations significantly higher than those achieved with Av-VEGF were associated with less toxicity. It is conceivable that the inability of KDR$^{sel}$ to induce the full complement of VEGF target genes, which includes inflammatory cytokines like IL-6, may account for such difference. Conversely, Flt$^{sel}$ did not induce angiogenesis or significant growth of the liver, although in the acute liver toxicity model, this molecule salvaged hepatocytes and organ function to an impressive extent. Indeed, one of the most striking conclusions of this study is that, following an appropriate signal, quiescent endothelium can be instructed to produce factors that can profoundly protect the parenchyma from injury. This is the first evidence that protective effects on parenchymal cells mediated by the endothelium can be uncoupled from stimulation of angiogenesis.

Given that the known dose-limiting effects of VEGF (e.g. hypotension, edema) (Yang et al., 1998) are associated with VEGFR-2 activation (Kliche and Waltenberger, 2001), it is contemplated that VEGFR-1 agonists such as Flt$^{sel}$ are useful in forming the basis of a therapeutic scheme aimed toward liver protection. The addition of a VEGFR-2 agonist or other angiogenic factor at a lower ratio may result in a maximal therapeutic benefit, by providing stimulation of angiogenesis. Alternatively, a VEGF mutant that preferentially activates VEGFR-1 versus VEGFR-2 might combine optimal characteristics of safety and efficacy. The potential indications include acute liver damage induced by various drugs, chemotherapy, or toxins as well as chronic injury, including cirrhosis.

Interestingly, although weights of organs such heart and kidney were also higher in VEGF-expressing animals relative to controls, this effect was smaller than in the liver and, importantly, only liver tissue was shown to exhibit a substantially increased proportion of cells that had undergone DNA synthesis. It is noteworthy that induction by VEGF or VEGFR-1 agonists of HGF, IL-6 and some other genes identified in this study is not a general response of endothelial cells; HUVEC or murine lung endothelial cells failed to show any induction of such genes. Therefore, such an endothelial dependent paracrine growth promoting mechanism in response to an ubiquitous molecule like VEGF is, at least in part, restricted to LSEC and may be another facet of the influence of the "microenvironment" on organ diversity (Dellian et al. (1996) *Am. J. Pathol.* 149:59-71). Previous studies have reported the existence of an angiogenic mitogen, with a selectivity for a specific type of endothelium (LeCouter et al. (2001) *Nature* 412:877-884). It is tempting to speculate that the vascular endothelium of other organs may be triggered to release tissue-specific growth factors in response to more selective "keys" than VEGF.

Finally, recent studies have linked liver organogenesis to potential inductive signals originating in the endothelium, prior to establishment of blood flow and vascular functions (Matsumoto et al., 2001). It is tempting to speculate that the mechanism described herein may, at least in part, provide an explanation for such inductive events.

What is claimed is:

1. A method for promoting liver growth in a subject, comprising administering to the subject an effective amount of a VEGFR modulating agent that comprises placental growth factor (PlGF), wherein the liver mass of the subject is increased.

2. The method of claim 1, further comprising administering VEGF in an amount effective to promote proliferation of nonparenchymal cells in the liver.

3. The method of claim 1, wherein the VEGFR modulating agent is administered to the subject through a systemic delivery system comprising said VEGFR modulating agent and a polymer matrix, wherein said polymer matrix is a liposome, microsphere, microemulsion, nanoparticle or nanocapsule.

4. The method of claim 1, wherein the VEGFR modulating agent is administered via a liver-targeted adenoviral vector comprising a nucleic acid encoding the VEGFR modulating agent.

5. A method for promoting hepatocyte proliferation in the liver of a subject, comprising administering to the subject a Flt-1 agonist comprising placental growth factor (PlGF), in a manner effective to promote hepatocyte proliferation.

6. The method of claim 5, wherein the Flt-1 agonist is delivered to the nonparenchymal cells of the liver.

7. The method of claim 6, wherein the nonparenchymal cells are sinusoidal endothelial cells.

8. The method of claim 5, wherein the Flt-1 agonist is administered to the subject through a systemic delivery system comprising a slow release preparation comprising said Flt-1 agonist and a polymer matrix, wherein said polymer matrix is a liposome, microsphere, microemulsion, nanoparticle and nanocapsule.

9. The method of claim 5, wherein the Flt-1 agonist is administered via a liver-targeted adenoviral vector comprising a nucleic acid encoding the Flt-1 agonist.

10. The method of claim 1, further comprising administering VEGF in an amount effective to promote proliferation of nonparenchymal cells in the liver, wherein said PlGF is purified and is administered to the subject through a systemic delivery system comprising said PlGF and a polymer matrix, wherein said polymer matrix is a liposome, microsphere, microemulsion, nanoparticle or nanocapsule.

11. The method of claim 1, further comprising administering VEGF in an amount effective to promote proliferation of nonparenchymal cells in the liver, wherein said PlGF is administered via a liver-targeted adenoviral vector comprising a nucleic acid encoding said PlGF.

12. The method of claim 2, wherein said VEGF is $VEGF_{165}$.

13. The method of claim 10, wherein said VEGF is $VEGF_{165}$.

14. The method of claim 11, wherein said VEGF is $VEGF_{165}$.

* * * * *